US008920870B2

(12) United States Patent
Weber

(10) Patent No.: US 8,920,870 B2
(45) Date of Patent: Dec. 30, 2014

(54) VARIABLE STIFFNESS CATHETER ASSEMBLY

(75) Inventor: Jan Weber, Maple Grove, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1067 days.

(21) Appl. No.: 12/847,703

(22) Filed: Jul. 30, 2010

(65) Prior Publication Data

US 2010/0297334 A1 Nov. 25, 2010

Related U.S. Application Data

(63) Continuation of application No. 11/411,360, filed on Apr. 25, 2006, now Pat. No. 7,766,896.

(51) Int. Cl.
*A61M 25/10* (2013.01)
*B05D 3/12* (2006.01)
*A61M 25/00* (2006.01)
*A61M 25/09* (2006.01)
*A61M 25/01* (2006.01)

(52) U.S. Cl.
CPC ....... *A61M 25/0054* (2013.01); *A61M 25/0009* (2013.01); *A61M 25/1006* (2013.01); *A61M 2025/0039* (2013.01); *A61M 2025/0024* (2013.01); *A61M 25/0053* (2013.01); *A61M 2025/0063* (2013.01); *A61M 25/0045* (2013.01); *A61M 2025/09175* (2013.01); *A61M 25/0138* (2013.01); *A61M 2025/0915* (2013.01); *A61M 2025/0058* (2013.01); *A61M 2025/0035* (2013.01); *A61M 25/0158* (2013.01); *A61M 25/09* (2013.01)
USPC ........... 427/2.28; 427/2.1; 427/2.24; 604/527

(58) Field of Classification Search
None
See application file for complete search history.

(56) References Cited

U.S. PATENT DOCUMENTS

| 4,321,226 | A | * | 3/1982 | Markling | 264/139 |
| 4,443,277 | A | * | 4/1984 | Rokas | 156/50 |
| 4,764,324 | A | * | 8/1988 | Burnham | 264/103 |
| 5,573,520 | A | | 11/1996 | Schwartz et al. | |
| 5,855,565 | A | | 1/1999 | Bar-Cohen et al. | |
| 6,024,764 | A | * | 2/2000 | Schroeppel | 606/198 |
| 6,109,852 | A | | 8/2000 | Shahinpoor et al. | |
| 6,117,296 | A | | 9/2000 | Thomson | |
| 6,249,076 | B1 | | 6/2001 | Madden et al. | |
| 6,379,393 | B1 | | 4/2002 | Mavroidis et al. | |
| 6,388,043 | B1 | | 5/2002 | Langer | |
| 6,514,237 | B1 | | 2/2003 | Maseda | |
| 6,620,527 | B2 | | 9/2003 | Wang | |
| 6,679,836 | B2 | | 1/2004 | Couvillon, Jr. | |
| 6,749,556 | B2 | | 6/2004 | Banik | |

(Continued)

FOREIGN PATENT DOCUMENTS

WO 2004014238 A2 2/2004

OTHER PUBLICATIONS

D Zhou et al., "Actuators for the Cochlear Implant," Synthetic Metals 135-136 (2003) 39-40.

(Continued)

*Primary Examiner* — Cachet Sellman
(74) *Attorney, Agent, or Firm* — Vidas, Arrett & Steinkraus, P.A.

(57) ABSTRACT

A catheter comprising an outer shaft comprising a first section of electroactive polymer. The first section of electroactive polymer affecting either the flexibility of the catheter or the steerability of the catheter.

19 Claims, 26 Drawing Sheets

(56) References Cited

U.S. PATENT DOCUMENTS

| | | |
|---|---|---|
| 6,770,027 B2 | 8/2004 | Banik et al. |
| 6,812,624 B1 | 11/2004 | Pei et al. |
| 6,835,173 B2 | 12/2004 | Couvillon, Jr. |
| 6,855,137 B2* | 2/2005 | Bon .................. 604/525 |
| 6,921,360 B2 | 7/2005 | Banik |
| 6,940,211 B2 | 9/2005 | Pelrine et al. |
| 6,982,514 B1 | 1/2006 | Lu et al. |
| 6,997,870 B2 | 2/2006 | Couvillon, Jr. |
| 7,193,350 B1 | 3/2007 | Blackburn et al. |
| 7,469,700 B2* | 12/2008 | Baran .................. 128/207.14 |
| 7,472,705 B2* | 1/2009 | Baran .................. 128/207.11 |
| 7,857,777 B2* | 12/2010 | Larson et al. .............. 602/13 |
| 8,016,752 B2* | 9/2011 | Armstrong et al. ........ 600/156 |
| 2003/0045920 A1 | 3/2003 | Belden et al. |
| 2003/0236445 A1 | 12/2003 | Couvillon, Jr. |
| 2004/0054322 A1 | 3/2004 | Vargas |
| 2004/0068161 A1* | 4/2004 | Couvillon .................. 600/143 |
| 2004/0068224 A1* | 4/2004 | Couvillon et al. .......... 604/67 |
| 2004/0087982 A1 | 5/2004 | Eskuri |
| 2004/0138733 A1 | 7/2004 | Weber et al. |
| 2004/0143160 A1 | 7/2004 | Couvillon, Jr. |
| 2005/0004425 A1 | 1/2005 | Banik |
| 2005/0070844 A1* | 3/2005 | Chow et al. ............... 604/95.04 |
| 2005/0085693 A1 | 4/2005 | Belson et al. |
| 2005/0102017 A1* | 5/2005 | Mattison .................. 623/1.11 |
| 2005/0107669 A1 | 5/2005 | Couvillon, Jr. |
| 2005/0165439 A1* | 7/2005 | Weber et al. .............. 606/191 |
| 2006/0030864 A1* | 2/2006 | Kennedy, et al. .......... 606/108 |
| 2006/0041264 A1 | 2/2006 | Eskuri |
| 2006/0069417 A1 | 3/2006 | Farley et al. |
| 2006/0084884 A1 | 4/2006 | Beatty et al. |
| 2006/0111618 A1 | 5/2006 | Couvillon, Jr. |
| 2007/0112331 A1 | 5/2007 | Weber |
| 2007/0208276 A1 | 9/2007 | Kornkven Volk |

OTHER PUBLICATIONS

E. Smela et al., "Thiol Modified Pyrrole Monomers: 1. Synthesis, Characterization, and Polymerization of 1-(2- Thioethyl)-Pyrrole and 3-(2-Thioethyl)-Pyrrole," Langmuir, 14 (11), 2970-2975, 1998.

E.W.H. Jager, E. Smela, O. Inganas, "Microfabricating Conjugated Polymer Actuators," Science, 290, 1540-1545, 2000.

E. Smela, M. Kallenbach, and J. Holdenried, "Electrochemically Driven Polypyrrole Bilayers for Moving and Positioning Bulk Micromachined Silicon Plates," J. Microelectromechanical Systems, 8(4), 373-383, 1999.

Proceedings of the SPIE, vol. 4329 (2001) entitled "Smart Structures and Materials" 2001. see Madden et al., "Polypyrrole actuators: modeling and performance," pp. 73-83.

\* cited by examiner

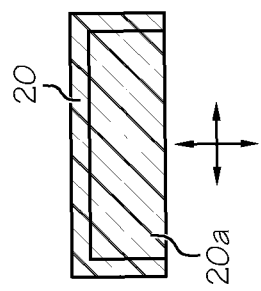
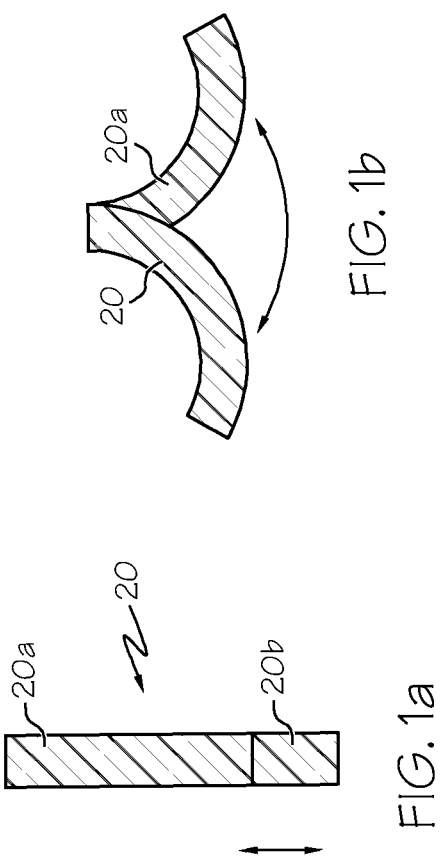

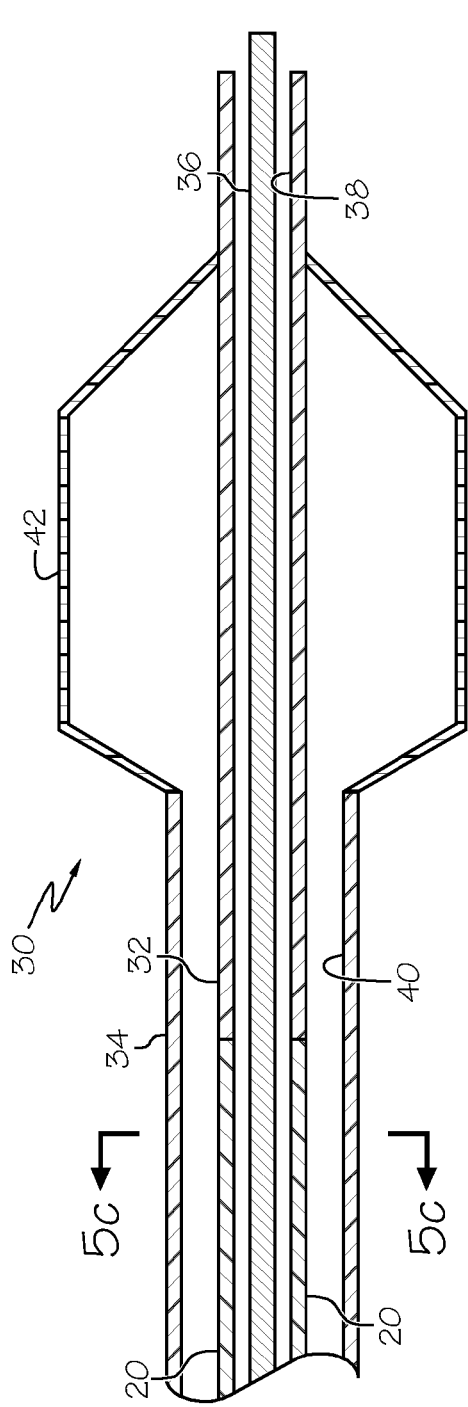
FIG. 5a
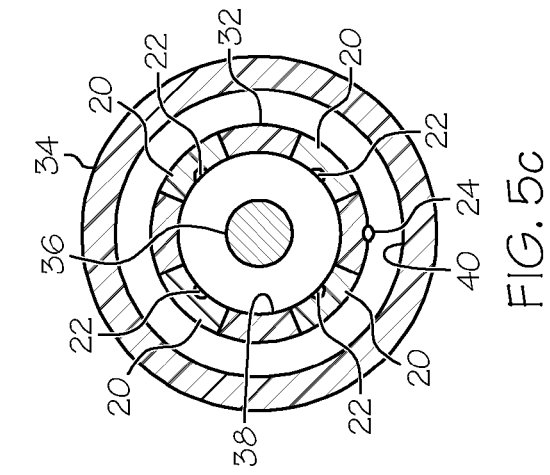
FIG. 5b
FIG. 5c

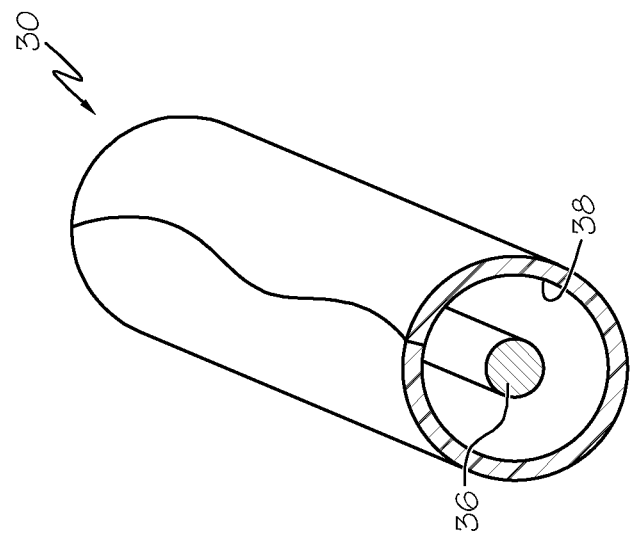
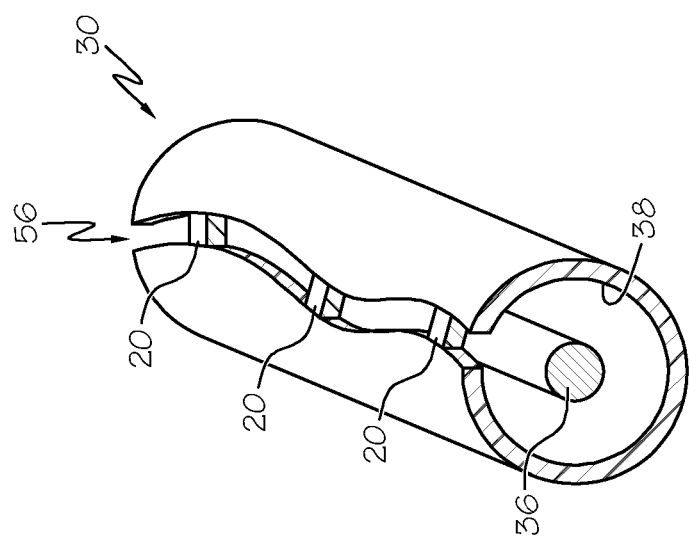

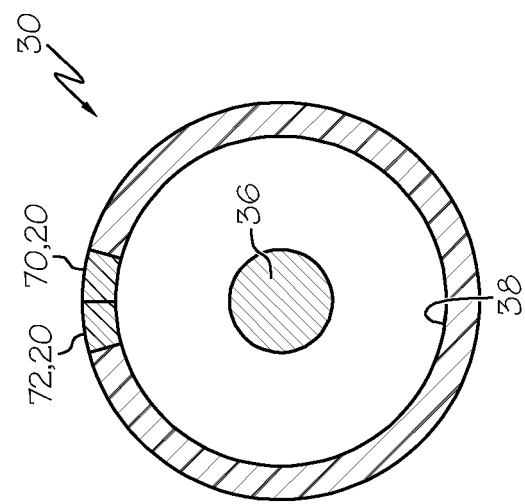
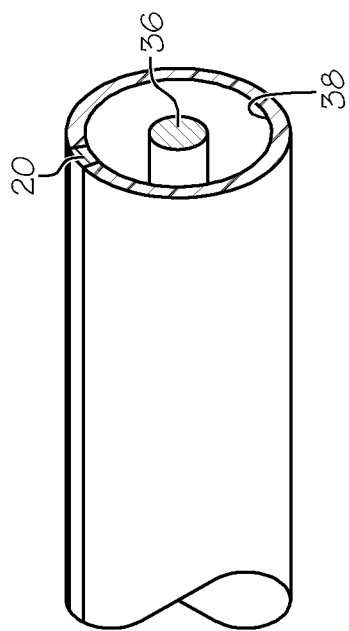
FIG. 7f
FIG. 7e

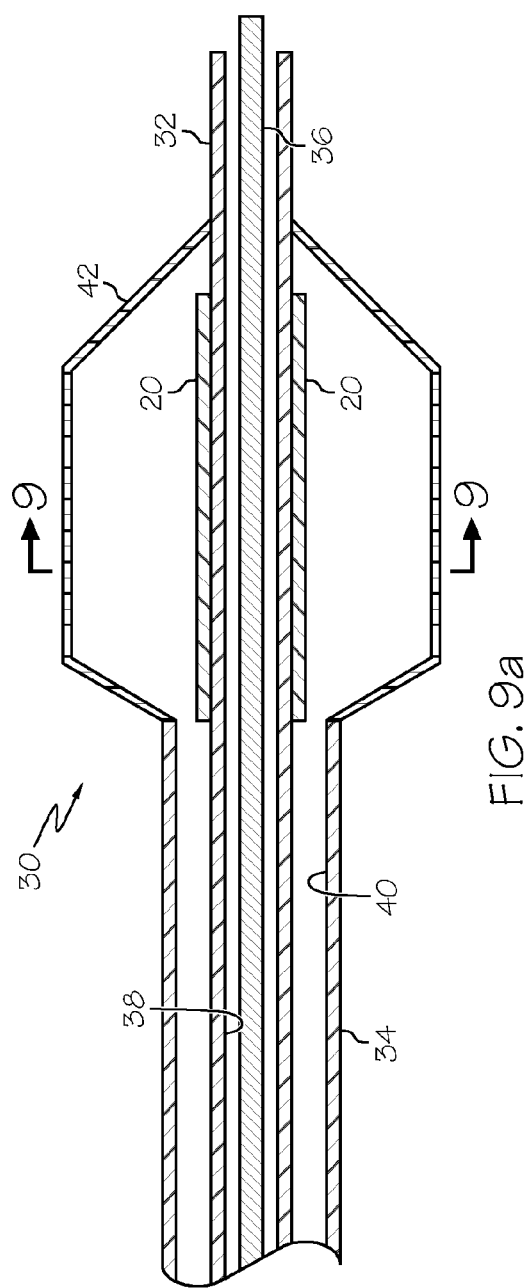
FIG. 9a
FIG. 9b
FIG. 9c

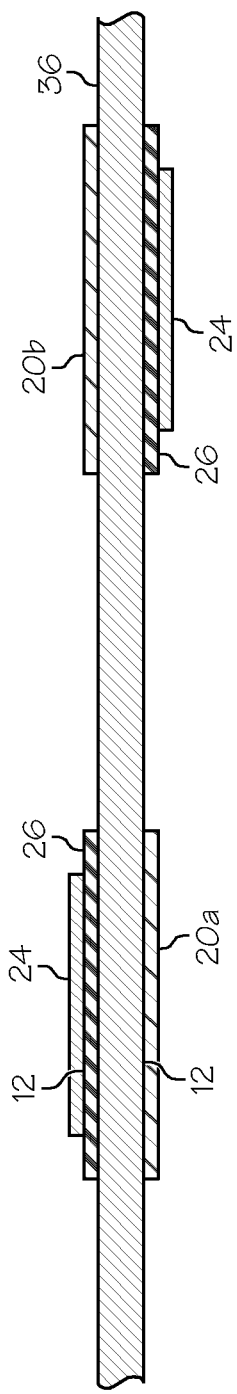
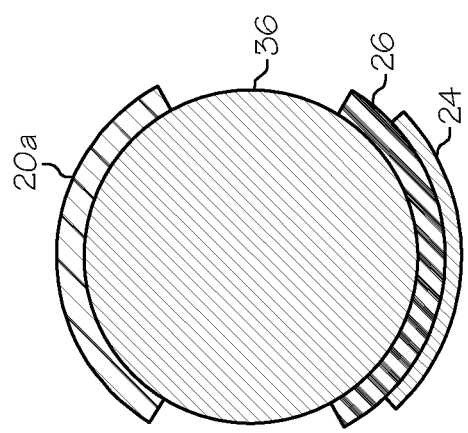

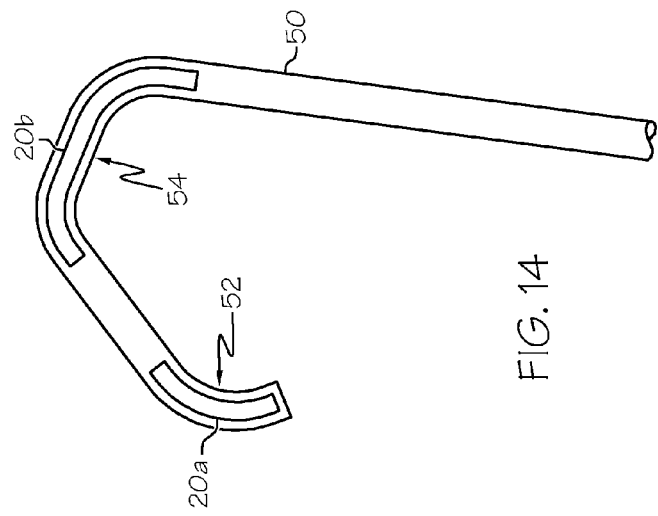
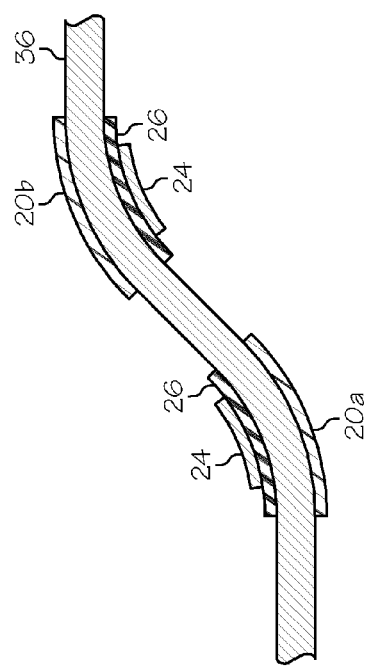

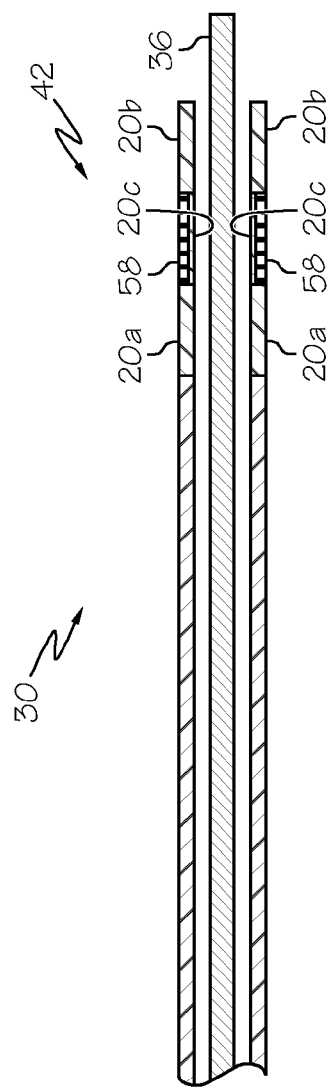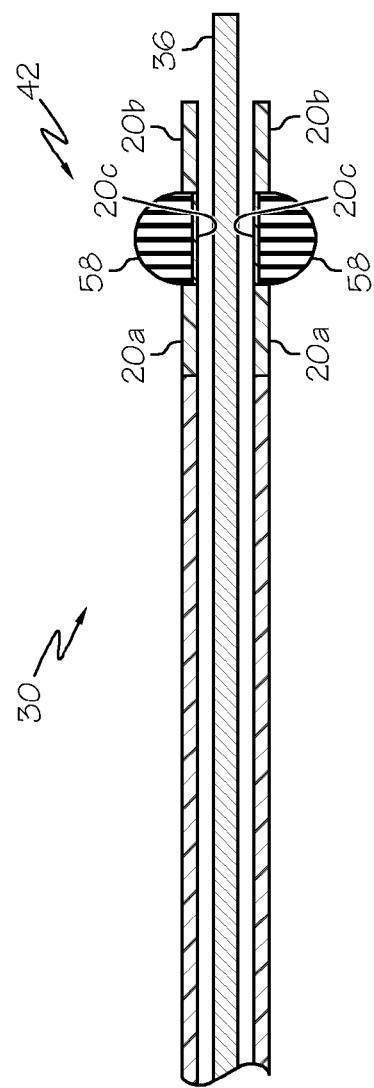

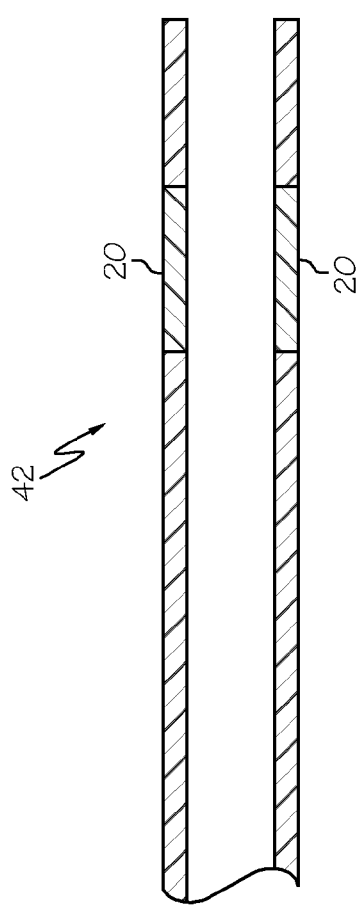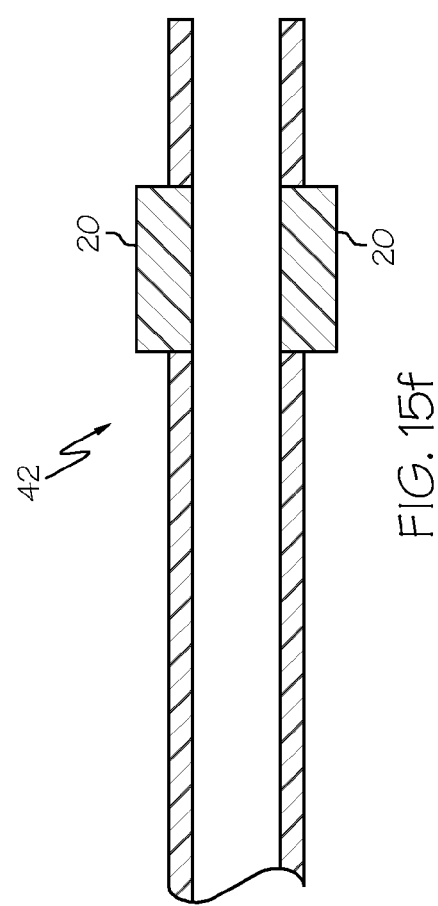

VARIABLE STIFFNESS CATHETER ASSEMBLY

CROSS-REFERENCE TO RELATED APPLICATIONS

This Application is a continuation of application Ser. No. 11/411,360, filed Apr. 25, 2006, and issued as U.S. Pat. No. 7,766,896 on Aug. 3, 2010.

STATEMENT REGARDING FEDERALLY SPONSORED RESEARCH

Not Applicable

FIELD OF THE INVENTION

The present invention relates generally to intravascular catheters for performing medical procedures.

BACKGROUND OF THE INVENTION

Intravascular catheters are currently utilized in a wide variety of minimally-invasive or percutaneous medical procedures. Generally, an intravascular catheter enables a physician to remotely perform a medical procedure by inserting the catheter into the vascular system of the patient at an easily accessible location and navigating the tip of the catheter to a desirable target site. By this method, virtually any target site in the patient's vascular system may be remotely accessed.

Typically, a percutaneous procedure begins with the step of inserting a distal portion of the catheter into the patient's vasculature at a convenient location. Once the distal portion of the catheter has entered the patient's vascular system the physician may urge the distal tip forward by applying forces to the proximal portion of the catheter. Typically, the path taken by a catheter through the vascular system is tortuous, requiring the catheter to change direction frequently. While advancing the catheter through the tortuous path of the patient's vasculature, the physician must steer the distal end of the catheter. During a percutaneous procedure, the physician typically is not able to manipulate the distal portion of the catheter directly. For this reason, physicians typically must steer the distal end of the catheter by applying torsional forces to the proximal portion of the catheter.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R.1.72. The abstract is not intended to be used for interpreting the scope of the claims.

BRIEF SUMMARY OF THE INVENTION

The present invention relates to strategic placement of sections of electroactive polymer (EAP) on a catheter shaft to provide the catheter with variable properties. When EAP is actuated, the EAP can volumetrically expand in size, volumetrically contract in size and consequently hinge, bend, rotate, expand, or contract the structural element with which the EAP is in connection.

In one aspect, the present invention relates to a catheter that has variable stiffness due to the strategic placement of at least one section of EAP at different locations on the catheter. Actuation of the at least one section of EAP causes the region surrounding the EAP section to increase in stiffness, thereby increasing the pushability of the catheter. Alternatively, actuation of the at least one section of EAP causes the region surrounding the EAP section to decrease in stiffness, thereby increasing flexibility of the catheter. In one embodiment, the at least one section of EAP forms part of either the inner or outer shaft. In one embodiment, the at least one section of EAP is a longitudinal strip. In one embodiment, the catheter shaft is manufactured of EAP. In one embodiment, the at least one section of EAP forms the outer surface of the inner shaft. In one embodiment, the at least one section of EAP is located in the catheter tip. In one embodiment, a braid is used as the electrode for the at least one EAP section in the variable stiffness catheter. In one embodiment, the EAP allows for better wire movement and flexibility. In at least one embodiment, at least one section of EAP volumetrically contracts when actuated so that the balloon remains taut when other portions of the catheter are manipulated to improve the catheter's pushability.

In one aspect, the invention relates to a catheter that has an improved capability to navigate the vasculature system due to strategic positioning of at least one section of EAP at different locations on the catheter. In one embodiment, at least one section of EAP is positioned on the inner shaft. In one embodiment, at least one section of EAP is located only on one side of the inner shaft to control the deflection of the distal tip. In one embodiment, at least one section of EAP changes the spatial configuration of the catheter to improve steering around corners. In one embodiment, the guidewire has at least one section of EAP. In one embodiment, the guide catheter has at least one section of EAP. In one embodiment, the catheter tip has at least one section of EAP. In one embodiment, the at least one section of EAP in an actuated state causes the PT guidewire to contract axially.

BRIEF DESCRIPTION OF THE SEVERAL VIEWS OF THE DRAWING(S)

A detailed description of the invention is hereafter described with specific reference being made to the drawings.

FIG. 1a depicts how EAP can increase or decrease from an initial length when actuated FIG. 1b depicts how EAP can bend when actuated.

FIG. 1c depicts how EAP can increase or decrease from an initial size when actuated.

FIG. 4c is a cross section of the embodiment of FIG. 4a.

FIG. 5a a longitudinal cross section of a catheter with strips of electroactive polymer forming a portion of the inner shaft.

FIG. 5b is a portion of the catheter shown in FIG. 5a, with the strips of electroactive polymer in an actuated state.

FIG. 5c is a cross-section of the catheter in FIG. 5a taken at line 5c-5c.

Figure 6A:
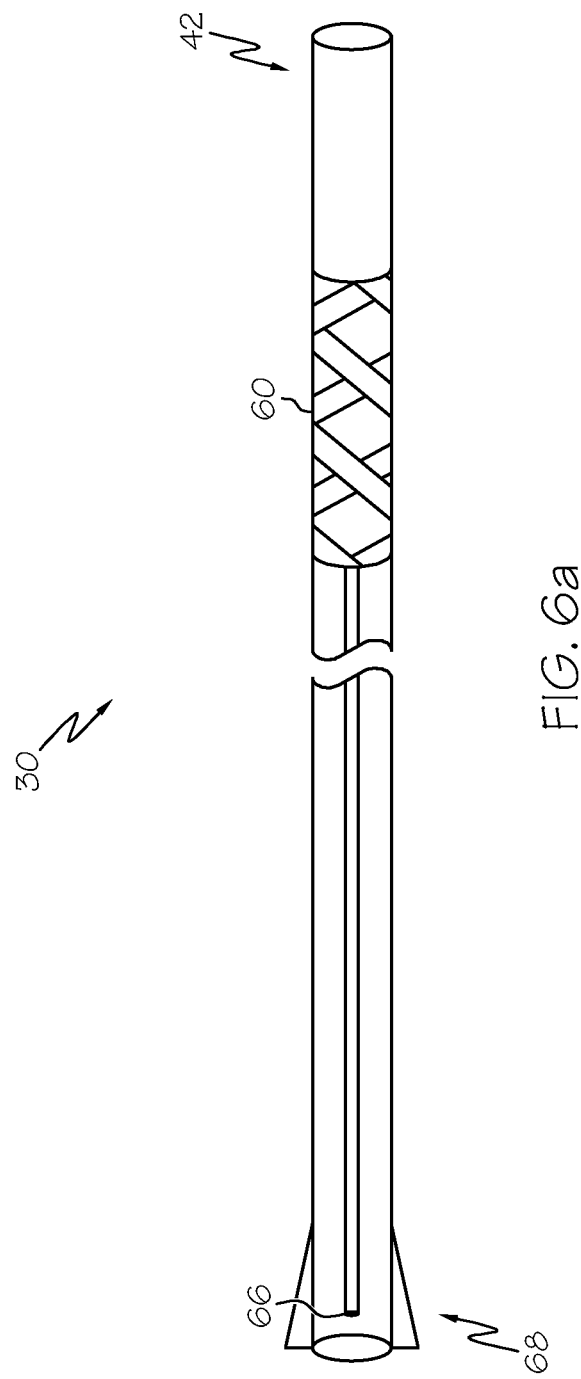

FIG. 6a is a flat plan of a braid with a loose pattern.

Figure 6B:
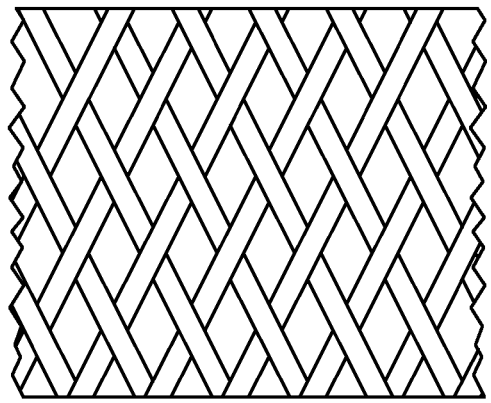

FIG. 6b is a flat plan of a braid with a dense pattern.

Figure 6C:
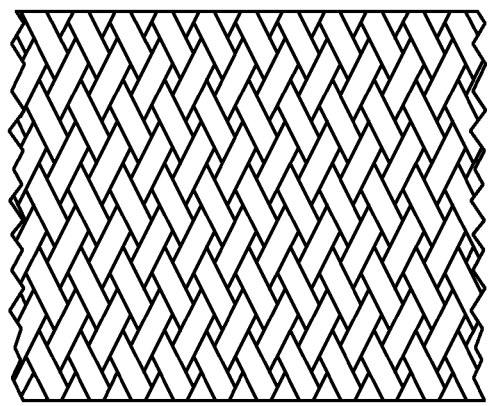

FIG. 6c is side view of the braided shaft of FIG. 6a forming a portion of a catheter.

Figure 6D:
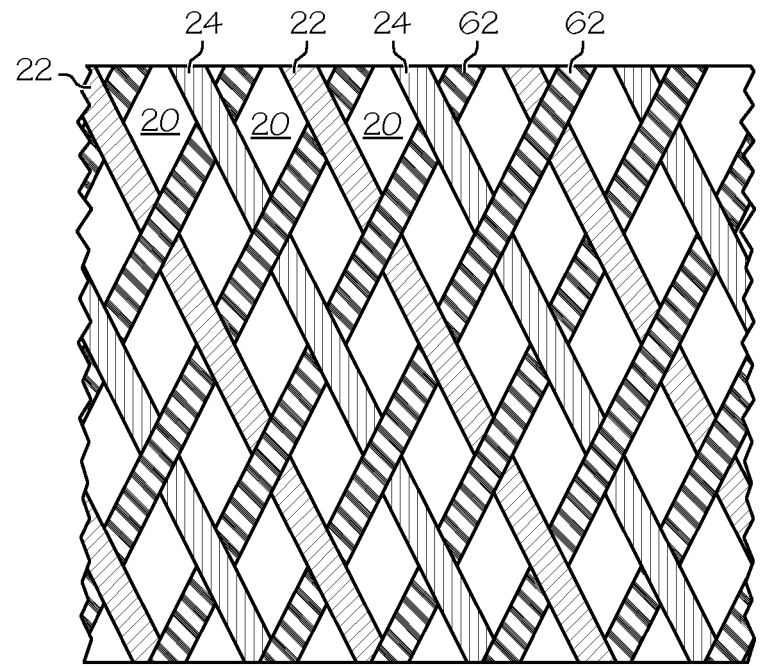

FIG. 6d is the flat plan of FIG. 6a with alternating electrode ribbons and counter electrode ribbons.

Figure 6E:
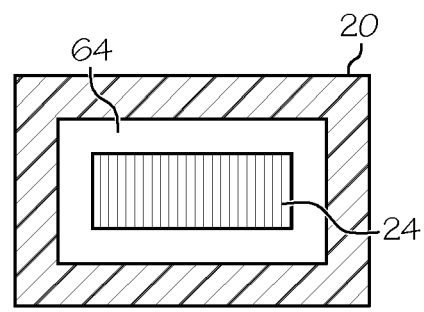

FIG. 6e is a cross-section of a ribbon with a layer of electroactive polymer about the circumference of the ribbon.

FIG. 7a is a portion of a catheter with a variable diameter due to a channel or slit with electroactive polymer in a non-actuated state.

FIG. 7b is the catheter of FIG. 7a with the electroactive polymer in an actuated state.

Figure 7D:
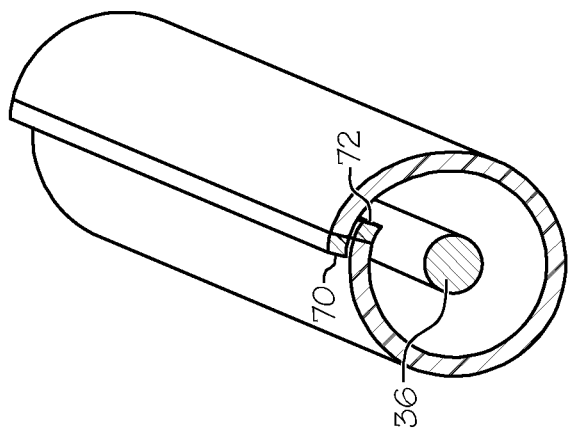
Figure 7C:
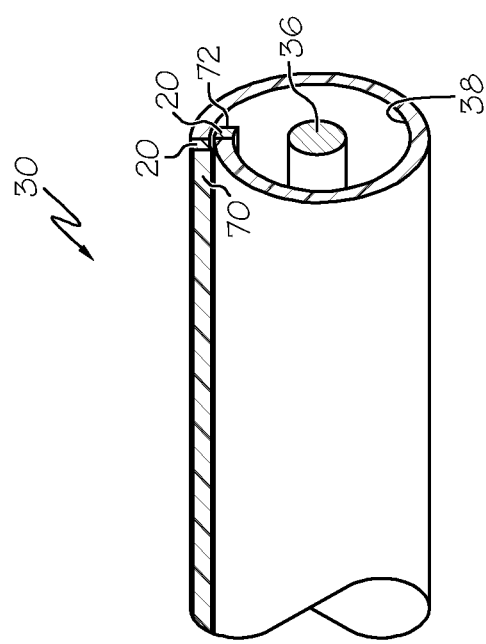

FIG. 7c is another embodiment of a catheter with a variable diameter with sections of electroactive polymer in an actuated state.

FIG. 7d is an end view of the catheter of FIG. 7c.

FIG. 7e is the catheter of FIG. 7c with the sections of electroactive polymer in a non-actuated state.

FIG. 7f is an end view of the catheter in FIG. 7e.

Figure 8A:
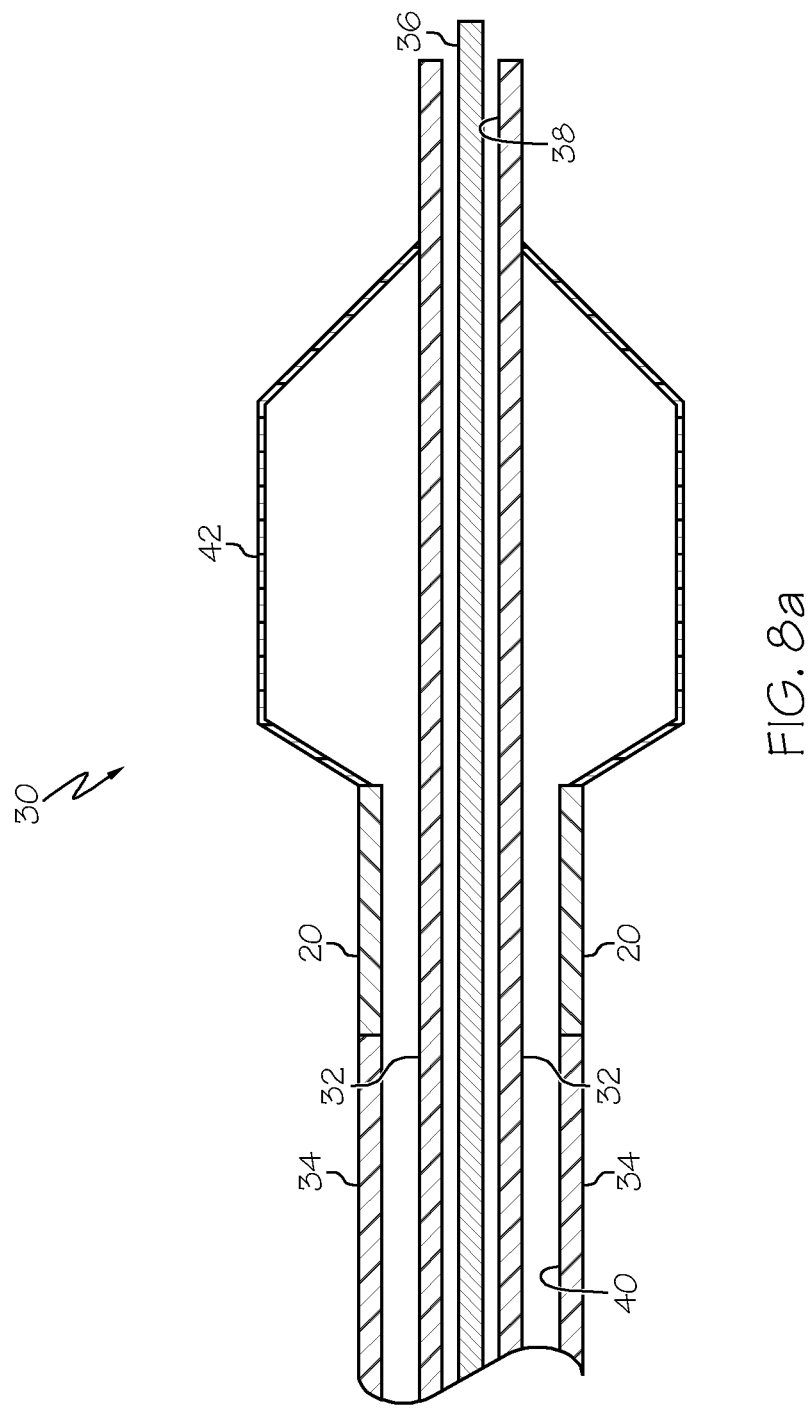

FIG. 8a is a longitudinal cross-section of the catheter in the non-actuated state.

Figure 8B:
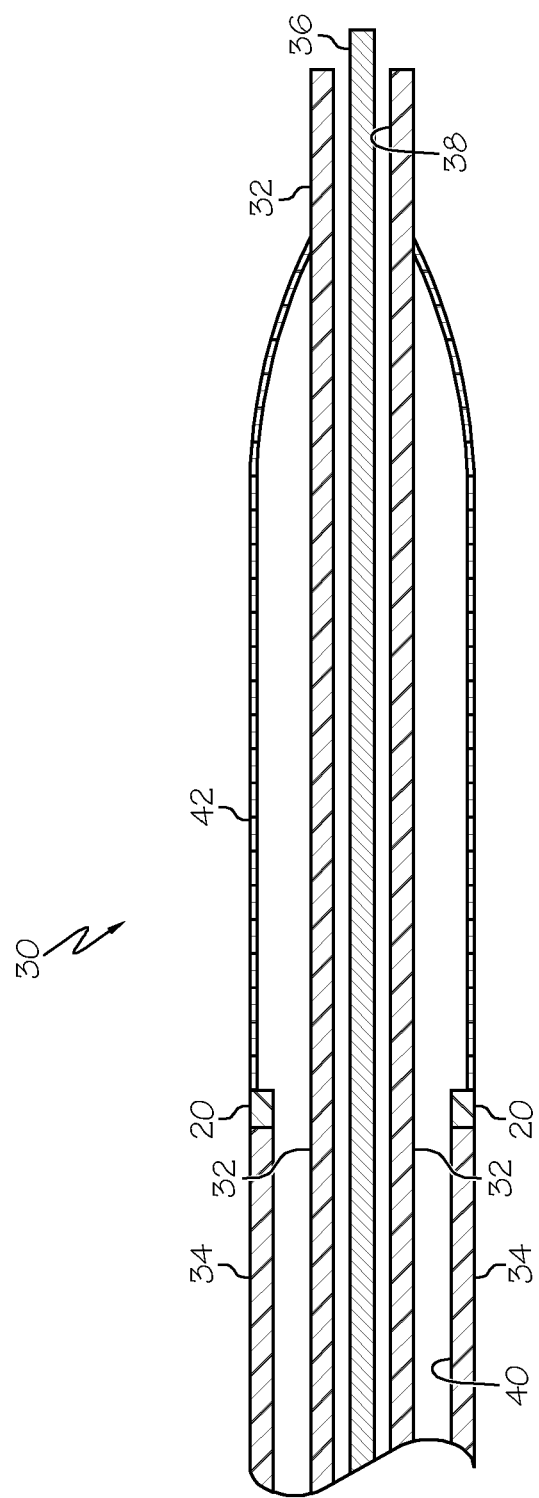

FIG. 8b is a longitudinal cross-section of the catheter in the actuated state in which the outer shaft has decreased in length (in the proximal direction).

FIG. 9a is a longitudinal cross-section of the catheter with strips of electroactive polymer in a non-actuated state.

FIG. 9b is a cross-section of the catheter in FIG. 9a taken at line 9-9.

FIG. 9c is a cross-section of the catheter in FIG. 9a taken at line 9-9 showing an embodiment where the strips of electroactive polymer form a portion of the wall of the inner shaft.

Figure 9D:
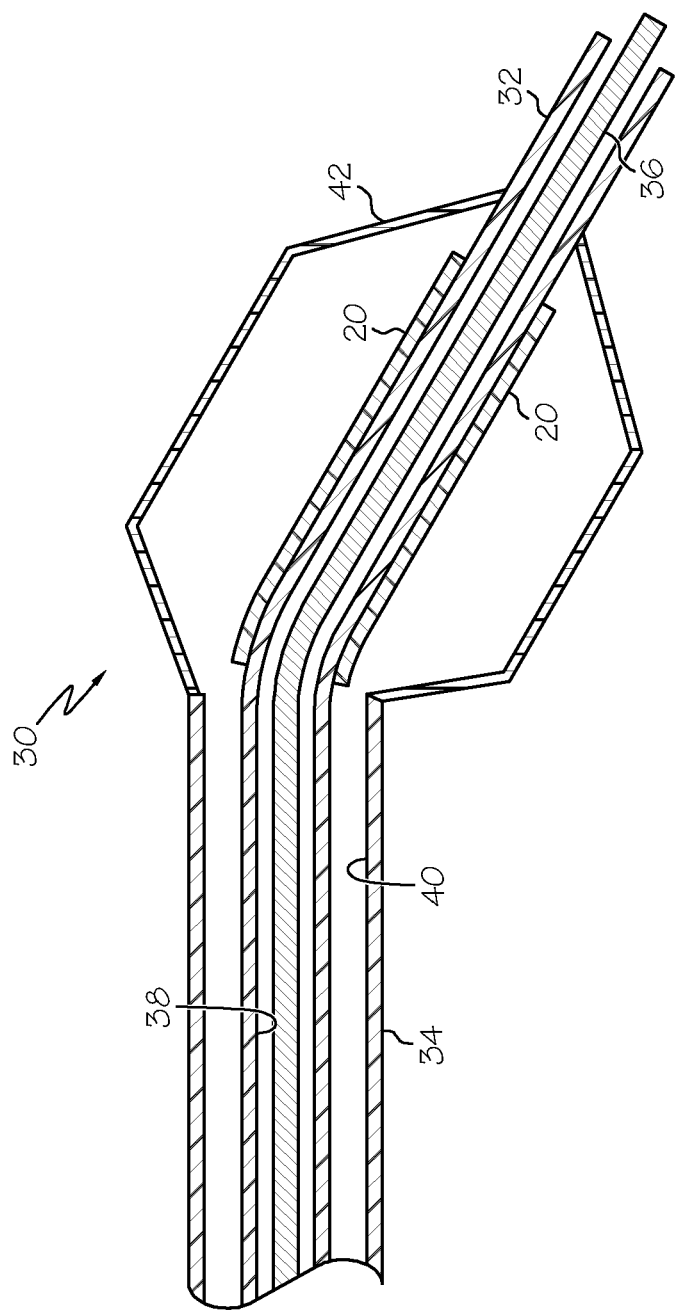

FIG. 9d the longitudinal cross-section of FIG. 9a with one strip of electroactive polymer in an actuated state thereby causing the catheter to bend.

Figure 10A:
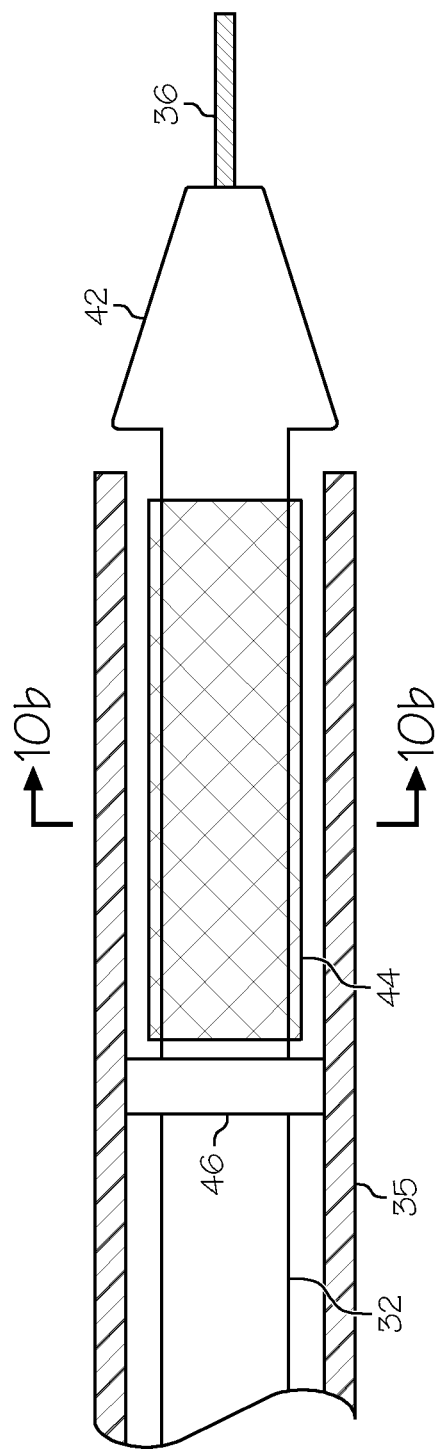

FIG. 10a is a longitudinal cross-section of a catheter where the inner shaft has at least one section of electroactive polymer positioned where the self-expanding stent is engaged to the inner shaft.

Figure 10B:
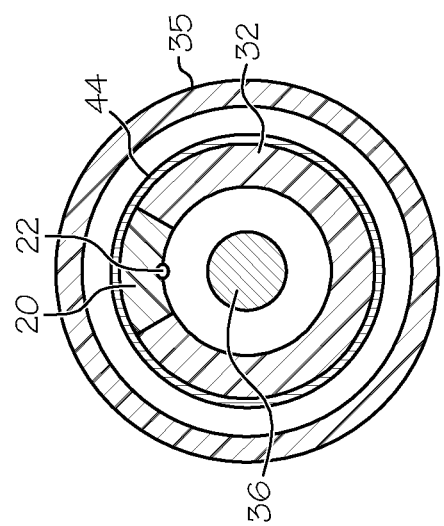

FIG. 10b is a cross-section of the catheter of FIG. 10a taken at line 10b-10b

Figure 11:
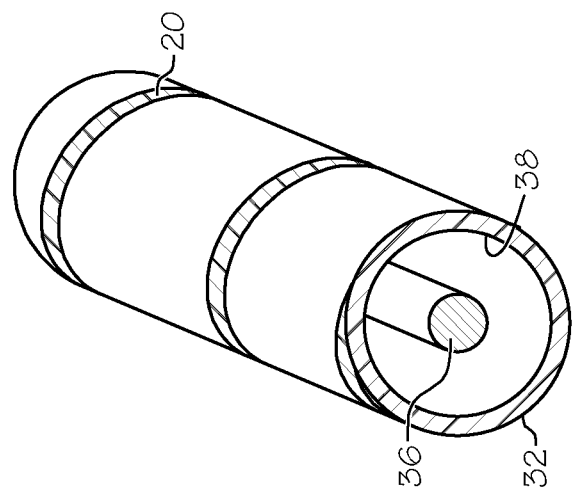

FIG. 11 is a cross section of the inventive catheter with at least one section of electroactive polymer in a spiral configuration about the catheter shaft.

Figure 12A:
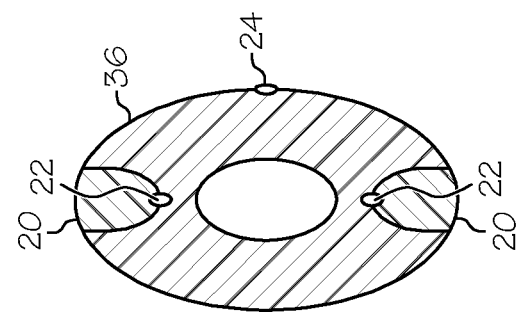

FIG. 12a is a cross section of the inventive catheter shaft with two longitudinal sections of electroactive polymer in a non-actuated state.

Figure 12B:
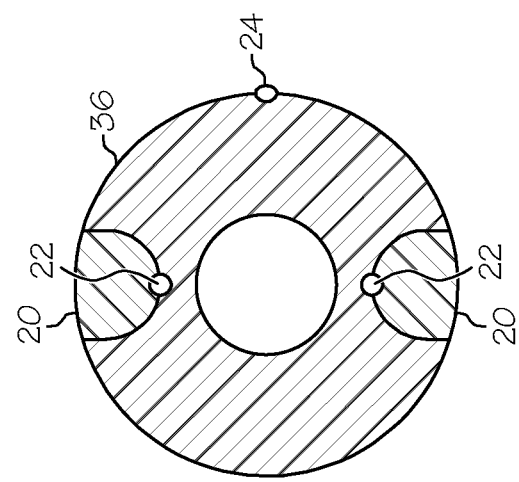

FIG. 12b is the cross section of FIG. 12a with the two longitudinal sections of electroactive polymer in an actuated state, causing the cross-sectional shape of the catheter to become more oval.

FIG. 13a is a guide wire with two separate axial sections of electroactive polymer.

FIG. 13b is a cross section of the guide wire in FIG. 13a taken at line 13-13.

FIG. 13c is the guide wire of FIG. 13a with one section of electroactive polymer in an actuated state, causing the guide wire to bend.

FIG. 14 is a guide catheter with two longitudinal sections of electroactive polymer.

Figure 15A:
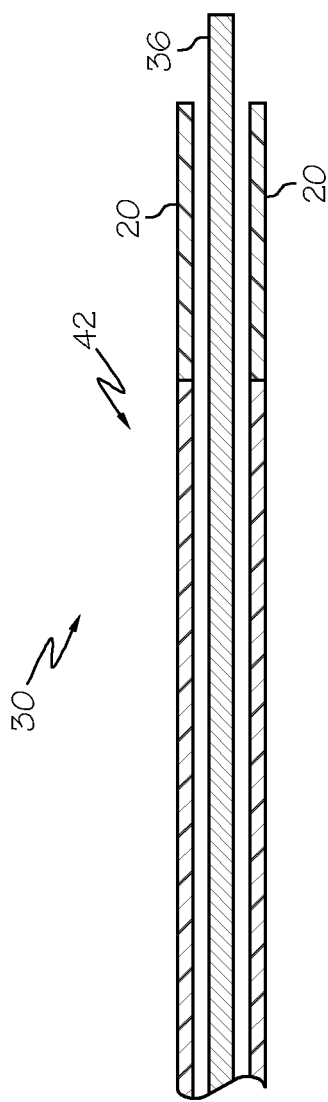

FIG. 15a is a longitudinal cross-section of the distal end portion of a catheter with at least one section of electroactive polymer at the distal end region.

Figure 15B:
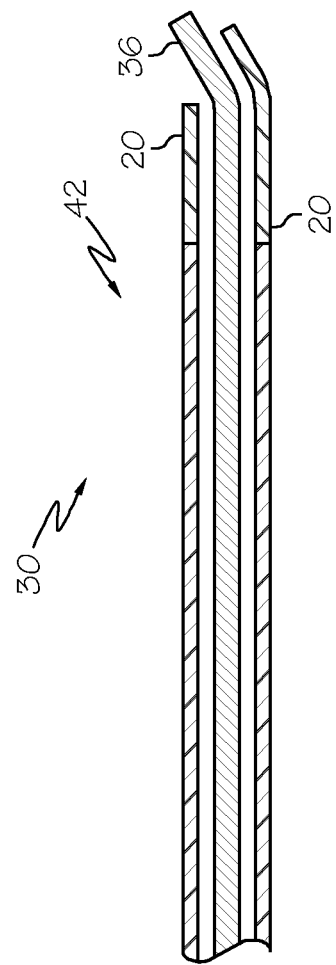

FIG. 15b is the cross-section of FIG. 15a with the at least one section of electroactive polymer in an acuated state.

FIG. 15c is a longitudinal cross-section of the distal end portion of a catheter with two circumferential bands of electroactive polymer in a non-actuated state.

FIG. 15d is the cross-section of FIG. 15c with the electroactive polymer in an actuated state.

FIG. 15e is a longitudinal cross section of the distal end portion of a catheter with a section of electroactive polymer in a non-actuated state.

FIG. 15f is the cross-section of FIG. 15e with the electroactive polymer in an actuated state.

Figure 16A:
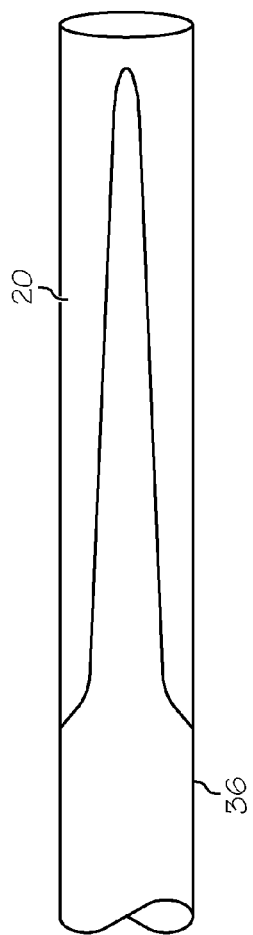

FIG. 16a is a longitudinal cross-section of a guide wire with a non-actuated section of electroactive polymer at the tip.

Figure 16B:
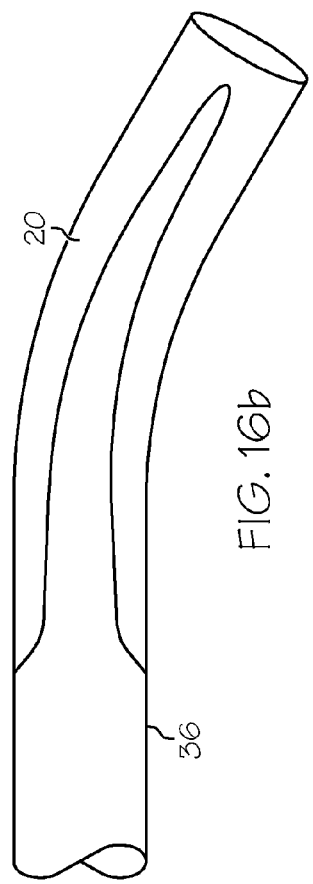

FIG. 16b is the cross-section of a guide wire of FIG. 16a with the section of electroactive polymer in an actuated state.

Figure 17B:
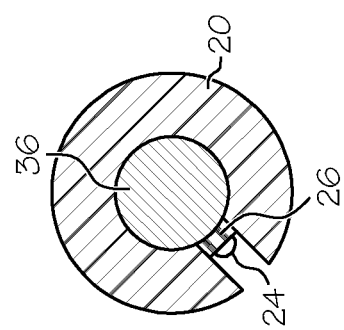
Figure 17A:
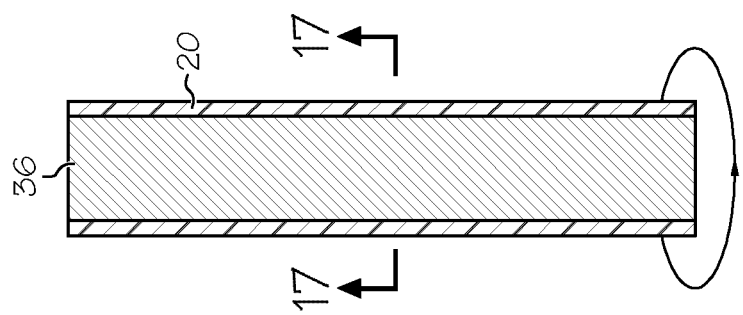

FIG. 17a depicts a guide wire with a layer of electroactive polymer that was deposited onto the guide wire while the guide wire was under a torsional force.

FIG. 17b depicts the rotation of the guide wire upon actuation of the layer of electroactive polymer.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

FIGS. 1a-c depict different ways EAP 20 can behave when actuated. All changes in the geometry of EAP 20, e.g. changing its linear length, are a result of the configuration of the EAP and the substrate it is put on. FIG. 1a depicts how EAP 20 can increase or decrease its linear length. When EAP 20a is actuated, the linear length increases, the additional length denoted by portion 20b. The EAP 20 may also be configured so that it decreases in length upon actuation. FIG. 1b shows how EAP 20 can bend when actuated with 20a denoting the EAP 20 prior to deformation and 20b denoting the EAP 20 after deformation. FIG. 1c depicts how EAP 20 can increase or decrease its bulk or size when actuated. When EAP 20a is actuated and increases its bulk or size when actuated, it goes from an initial size of 20a to an actuated size of 20. When EAP 20 is actuated and decreases its bulk or size when actuated, it goes from an initial size of 20 to an actuated size of 20a. Because actuation of EAP 20 is a linear process, if the activation of the EAP 20 is stopped somewhere between two end stages, fully oxidized and fully reduced, the EAP 20 will freeze at that particular state.

EAP is used in a variety of inventive ways disclosed herein. It has been discovered that EAP can be of particular importance in the design of catheters. In particular, EAP may be used in catheters to selectively alter the cross-section or shape of a catheter, to alter the stiffness of the catheter as well as in other ways discussed herein.

For purposes of illustration only, the catheter is depicted in the majority of figures as a balloon catheter. However it can be appreciated that the catheter can be any one of multiple different intravascular or non-intravascular catheter types. A person of ordinary skill in the art will be familiar with different types of catheters appropriate for multiple embodiments. Some examples of other intravascular catheters include, but are not limited to, diagnostic catheters, guide catheters, atherectomy catheters, stent delivery catheters, and the like.

In general, dilatation balloon catheters are preferably designed to optimize pushability, trackability, crossability, and torque transmission to the distal catheter end as such is applied to the proximal end of the catheter. In accordance with the present invention, pushability may be defined as the ability to transmit force from the proximal end of the catheter to the distal end of the catheter. A catheter shaft preferably has adequate strength for pushability and resistance to buckling or kinking Trackability may be defined for the purpose of this application as the ability to navigate tortuous vasculature. That is, the distal portion of the catheter preferably tracks the guide wire through small tortuous vessels to reach the area to be treated. A more flexible distal portion is known to improve such trackability. In accordance with the present invention, crossability may be defined as the ability to navigate the balloon catheter across narrow restrictions or obstructions in the vasculature.

The figures also show an example of where the electrode 22 and counter electrode 24 may be placed. These are merely examples of possible positions for the electrode and counter electrode 24. As explained herein and in commonly assigned U.S. patent application Ser. No. 10/763,825, the entire content of which is incorporated by reference herein, the counter electrode 24 is placed so that at least a portion of the surface of the counter electrode 24 is generally in contact with the electrolyte to facilitate the actuation of the section of EAP 20.

Figure 2A:
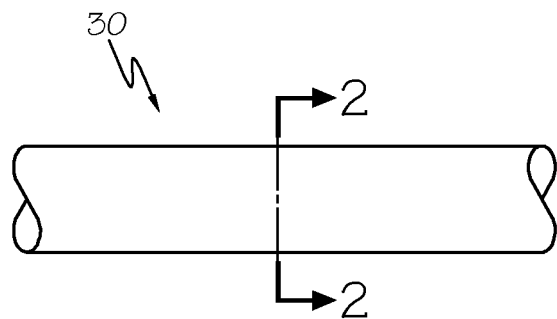
FIG. 2a is a side view of a portion of a catheter.
Figure 2B:
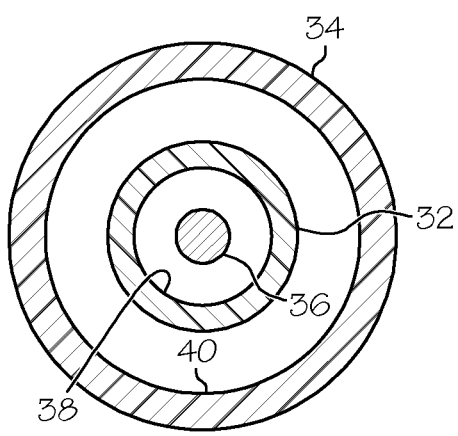
FIG. 2b is a cross-section of the catheter of FIG. 2a taken at line 2-2.

FIG. 2a shows a portion of a catheter 30. FIGS. 2b-2h show a cross section of the catheter 30 of FIG. 2a taken at line 2-2 in which the catheter 30 has a guide wire 36, an inner shaft 32, a guide wire lumen 38, an outer shaft 34 and an inflation lumen 40. The at least one section of EAP 20 may form a portion of only the inner shaft 32, only the outer shaft 34 or a portion of both the inner shaft 32 and the outer shaft 34. In FIG. 2b, the section(s) of EAP are in a non-actuated state. In the embodiments shown in FIGS. 2b-2d, the section of EAP 20 volumetrically expands when it is in an actuated state. Desirably, the region of the catheter 30 surrounding the at least one section of EAP 20 in an actuated state becomes more rigid and, in use, the pushability of the catheter 30 is improved. In the embodiments shown in FIGS. 2f-2h, the at least one section of EAP 20 volumetrically contracts when it is in an actuated state. Desirably, the region of the catheter 30 surrounding the at least one section of EAP 20 in an actuated state becomes more flexible and, in use, the trackability and deliverability of the catheter 30 is improved.

Figure 2C:
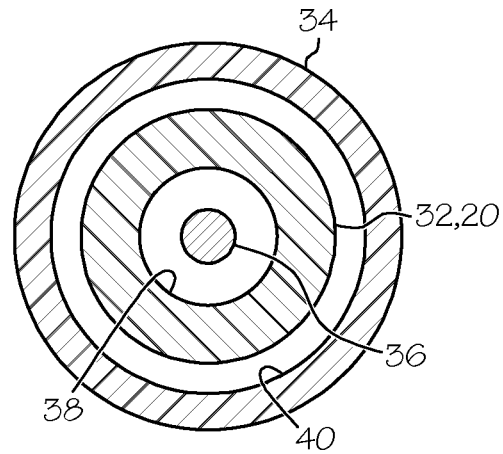
FIG. 2c is the cross-section of FIG. 2b showing the electroactive polymer of the inner shaft in an actuated state to improve pushability of the catheter.

In FIG. 2c, the at least one section of EAP 20 forming a portion of the inner shaft 32 is in an actuated state. Note that the size of the inflation lumen 40 in FIG. 2c has decreased, become smaller, compared to the size of the inflation lumen 40 in FIG. 2b when the EAP 20 is in a non-actuated state. The outer shaft 34 may also have EAP 20 which is in a non-actuated state since the section of EAP 20 in the inner shaft 32 can be actuated separately from the section of EAP 20 in the outer shaft 34.

Figure 2D:
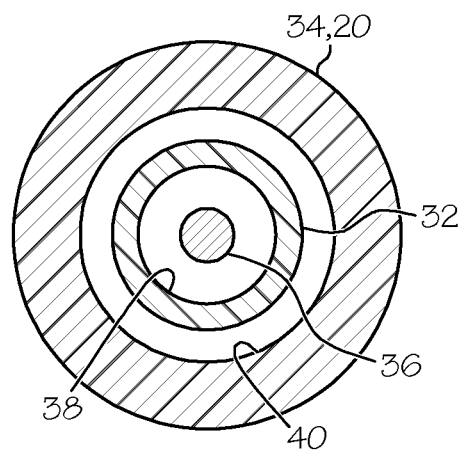
FIG. 2d is the cross-section of FIG. 2b showing the electroactive polymer of the outer shaft in an actuated state to improve pushability of the catheter.

In FIG. 2d the at least one section of EAP 20 forming a portion of the outer shaft 34 is in an actuated state. The inner shaft 32 may also have a section of EAP 20 in a non-actuated state since the section of EAP 20 on the inner shaft 32 may be actuated separately from the section of EAP 20 in the outer shaft 34. In the embodiment shown, actuation of the EAP 20 in the outer shaft 34 causes the inflation lumen 40 to decrease in size, become smaller, as compared to its size when the section of EAP 20 is in a non-actuated state, as in FIG. 2b. In one embodiment, actuation of the EAP in the outer shaft does not cause the inflation lumen to change in size, i.e. the section of EAP only expands in an outwardly direction.

Figure 2E:
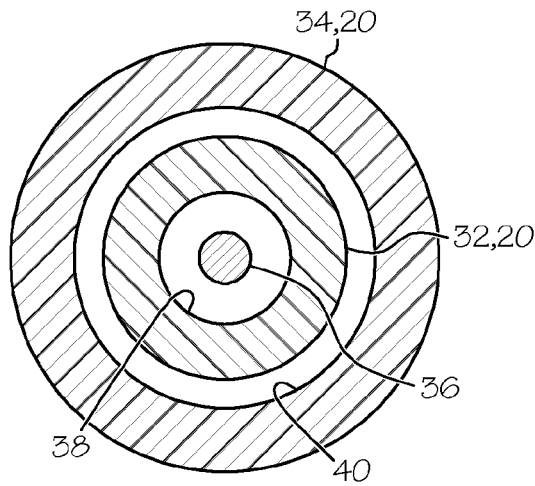
FIG. 2e is the cross-section of FIG. 2b showing the electroactive polymer of both the inner shaft and the outer shaft in an actuated state to improve pushability of the catheter.

In FIG. 2e, the sections of EAP 20 in both the inner shaft 32 and the outer shaft 34 are in an actuated state. In this embodiment, the inflation lumen 40 decreases in size due to the actuation of the EAP 20 in the inner shaft 32. In one embodiment, the inflation lumen decreases in size due to the actuation the sections of EAP in both the inner shaft and the outer shaft.

Figure 2F:
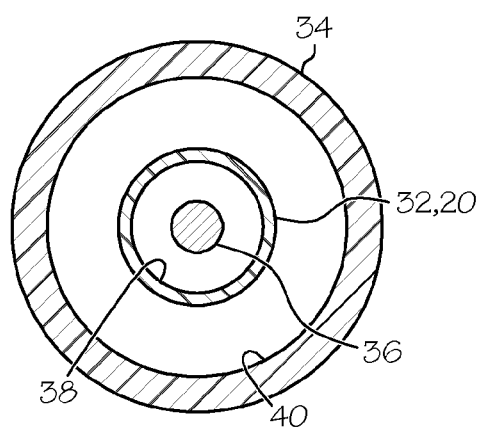
FIG. 2f is the cross-section of FIG. 2b showing the electroactive polymer of the inner shaft in an actuated state to improve flexibility of the catheter.

In the embodiment shown in FIG. 2f, the at least one section of EAP 20 in the inner shaft 32 is in an actuated state. Because the section of EAP 20 volumetrically contracts when actuated, the size of the inflation lumen 40 is larger as compared to the size of the inflation lumen 40 when the section of EAP 20 is in a non-actuated state. The outer shaft 34 can have a section of EAP 20 in a non-actuated state since the section of EAP 20 in the inner shaft 32 may be acutated separately from the section of EAP 20 in the outer shaft 34.

Figure 2G:
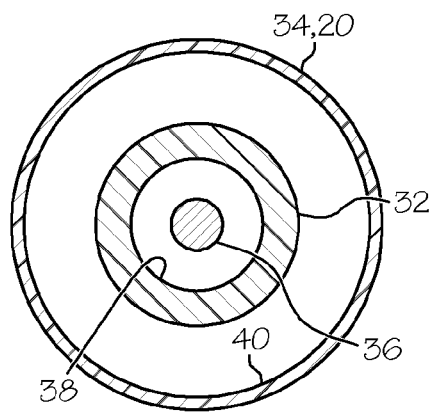
FIG. 2g is the cross-section of FIG. 2b showing the electroactive polymer of the outer shaft in an actuated state to improve flexibility of the catheter.

In FIG. 2g, the at least one section of EAP 20 of the outer shaft 34 is in an actuated state. The inner shaft 32 may have a section of EAP 20 in a non-actuated state since the section of EAP 20 in the inner shaft 32 may be actuated separately from the section of EAP 20 in the outer shaft 34.

Figure 2H:
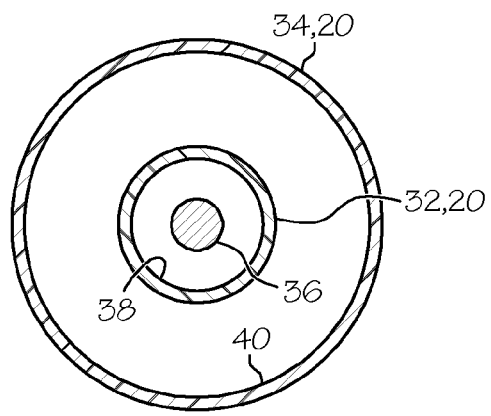
FIG. 2h is the cross-section of FIG. 2b showing the electroactive polymer of both the inner and outer shafts in an actuated state to improve flexibility of the catheter.

In FIG. 2h, the sections of EAP 20 in both the inner shaft 32 and outer shaft 34 are in an actuated state. Actuation of the section of EAP 20 in the inner shaft 32, causes the inflation lumen 40 to increase in size as compared its size when the section of EAP 20 is in a non-actuated state.

Figure 3A:
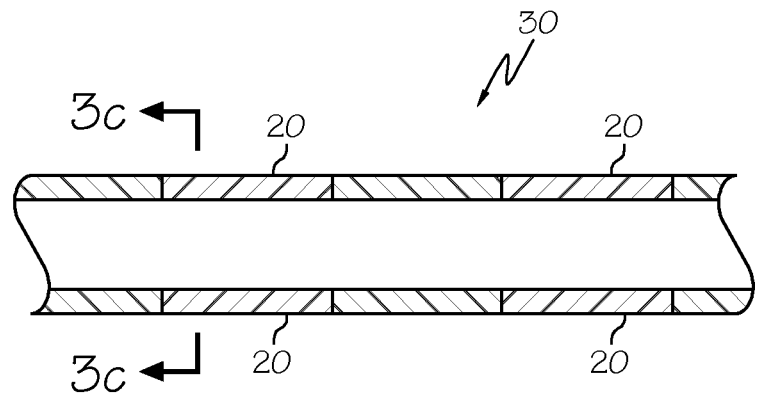
FIG. 3a is a longitudinal cross section of a catheter with strips of electroactive polymer forming a portion of the outer shaft.
Figure 3B:
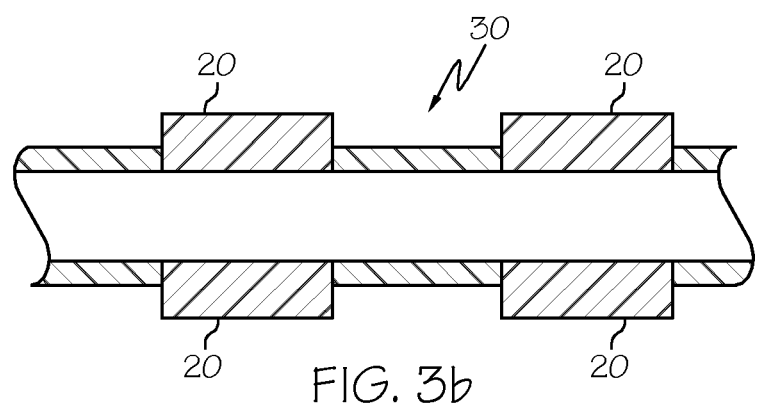
FIG. 3b is the catheter of FIG. 3a with the strips of electroactive polymer in an actuated state.

FIG. 3a depicts a longitudinal cross-section of a catheter 30 with a plurality of longitudinal strips of EAP 20 positioned about the circumference of the catheter shaft. In FIG. 3a, multiple strips of EAP 20, located at the same circumferential coordinate, are positioned along the longitudinal length of the catheter shaft. The exact placement about the circumference of the catheter shaft is not critical so long as the strips of EAP 20 are located about the entire circumference of the shaft along the area(s) where control of the flexibility/rigidity of the catheter shaft is desired. Desirably, actuation of the longitudinal strips of EAP 20 modifies the rigidity of the catheter shaft in the region of the EAP 20 strips. As shown in FIG. 3b, the longitudinal strips of EAP 20 volumetrically increase in size when actuated. Desirably, this will increase the stiffness and decrease the flexibility of the catheter. In one embodiment, the longitudinal strips of EAP volumetrically decrease in size when actuated. Desirably, this will decrease the stiffness and increase the flexibility of the catheter. In one embodiment, longitudinal strips of EAP 20 are positioned about the circumference of the catheter shaft and extend from the proximal end region of the catheter shaft to the distal end region of the catheter shaft. In addition, the number of strips of EAP 20 positioned about the circumference of the catheter shaft can vary. It is within the scope of the invention to have two, three, four, five, six, seven or eight longitudinal strips of EAP 20 positioned about the circumference of the catheter shaft and extending along a substantial portion of the catheter shaft. In one embodiment, the catheter shaft is manufactured from EAP 20.

Figure 3C:
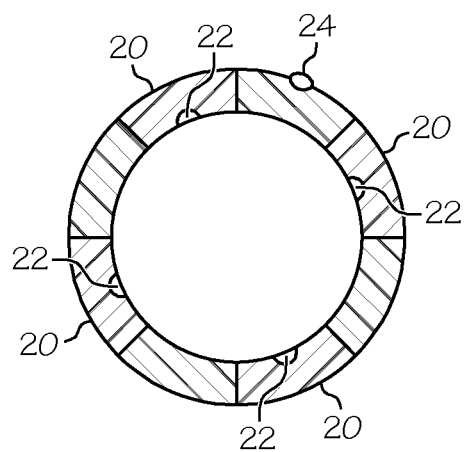
FIG. 3c is a cross-section of the embodiment of FIG. 3a taken at line 3c-3c.

The circumferential positions of the strips of EAP 20 are illustrated in FIG. 3c, which is a cross-section of the catheter 30 in FIG. 3a taken at line 3c-3c. The placement of the electrodes 22 and counter electrode 24 is more clearly seen in FIG. 3c. The electrodes 22 of different sections of EAP 20 are separate from one another so that precise actuation of the desired section(s) of EAP 20 can be done. As shown in FIGS. 3a and 3c, the exterior surface of the strip of EAP 20 is substantially flush with the exterior surface of the catheter shaft. Similarly, the interior surface of the strip of EAP 20, with the exception of the portion of the EAP 20 over the electrode 22, is substantially flush with the interior surface of the catheter shaft. However, in some embodiments of the invention, the strip of EAP 20 may form only a portion of the wall of the catheter shaft, i.e. the strip of EAP 20 does not have the same thickness as the wall of the catheter shaft and is not flush with either the exterior surface or the interior surface of the shaft.

Figure 4A:
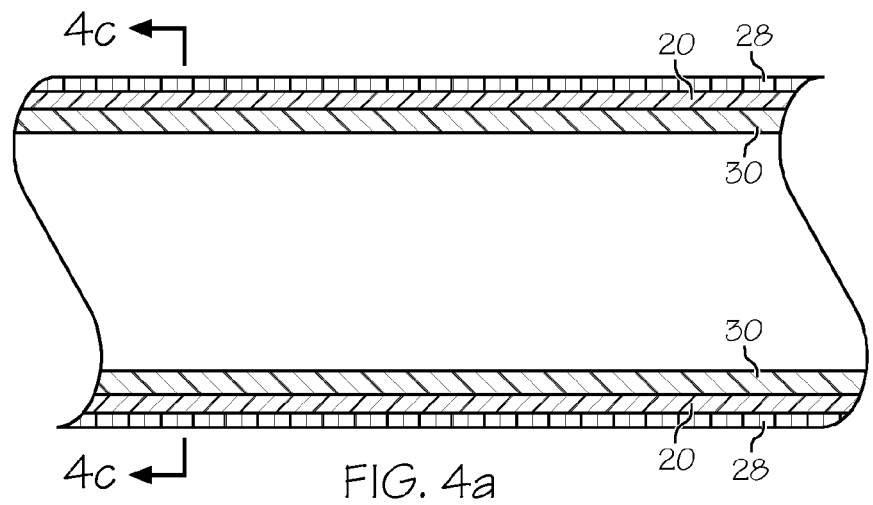
FIG. 4a is a longitudinal cross section of a catheter with a layer of electroactive polymer deposited on the outer shaft and stiff polymer strips deposited on the layer of electroactive polymer.
Figure 4B:
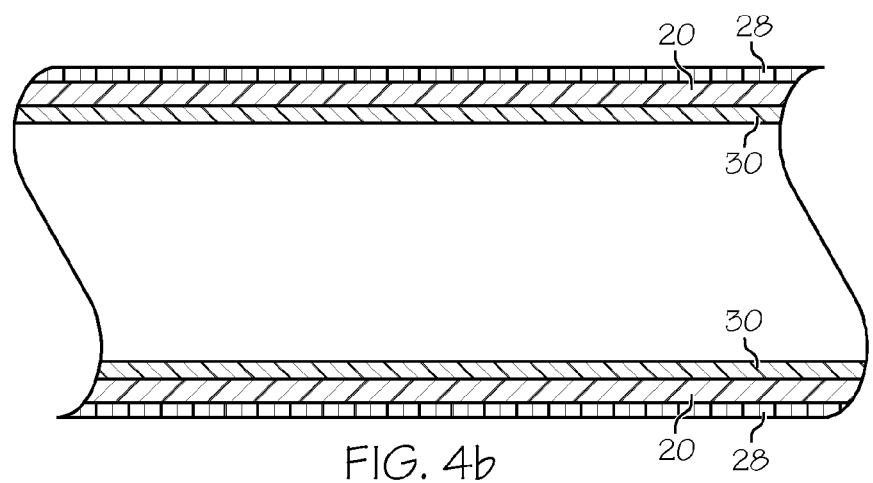
FIG. 4b is the longitudinal cross section of FIG. 4a with the layer of electroactive polymer in an actuated state.
Figure 4C:
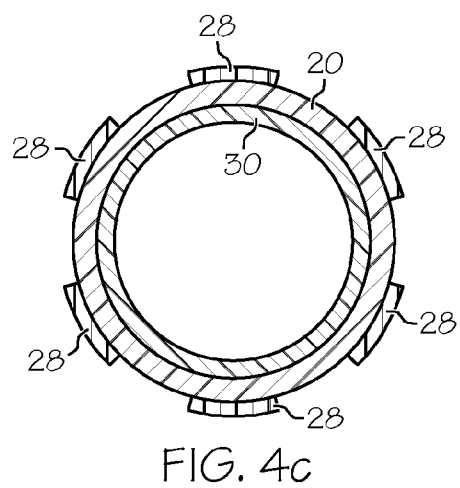

In one embodiment, shown in FIG. 4a-c, there are stiff elements, e.g. stiff polymer strips 28, engaged to a layer of EAP 20. If a catheter 30 with greater stiffness is desired, the layer of EAP 20 can be actuated. Actuation of the layer of EAP 20 causes the EAP 20 to volumetrically increase in size and moves the stiff polymer strips 28 further from the central axis of the catheter 30, as shown in FIG. 4b. Desirably, this causes an increase in the stiffness of the catheter 30 because the stiffness of a beam goes up with the fourth power of the size of the beam. In this embodiment, the layer of EAP is engaged to the outer surface of the catheter but the layer of EAP may be engaged to the outer surface of the outer shaft of a balloon catheter or other device for which the control of stiffness is desired.

As shown in FIG. 4c, there are six polymer strips 28 positioned about the circumference of the catheter 30. It is within the scope of the invention for there to be one, two, three, four, five, six, seven, eight, nine, ten or more polymer strips 28 about the circumference of the catheter 30. The polymer strips 28 may extend along the entire length of the catheter 30 or the strips 28 may be positioned at particular areas along the length of the catheter 30 where control of the stiffness of the catheter shaft is desired. Similarly, the layer of EAP 20 may extend along the entire length of the catheter 30 or the layer of EAP 20 may be placed at particular areas along the length of the catheter 30 where control of the stiffness of the catheter shaft is desired. In one embodiment, at least one portion of the catheter has a layer of EAP with at least one strip of stiff polymer engaged to the layer of EAP. Examples of suitable materials to be used for the stiff polymer strips include, but are not limited to, polyamides, polyethylene (PE), Marlex high density polyethylene, polyetheretherketone (PEEK), polyamide (PI), and polyetherimide (PEI), liquid crystal polymers (LCP), acetal and any mixtures or combinations thereof.

In the embodiment shown in FIG. 5a, strips of EAP 20 form a portion of the inner shaft 32. The balloon catheter in FIG. 5a has an outer shaft 34, an inner shaft 32, a guide wire 36 and a balloon 42. The inner shaft 32 defines a guide wire lumen 38. The outer shaft 34 defines an inflation lumen 40. Actuation of the strips of EAP 20 causes the strips of EAP 20 to expand. FIG. 5b shows the proximal portion of FIG. 5a. As depicted in FIG. 5b, actuation of the strips of EAP 20 will cause the inner shaft 32 to lock with the outer shaft 34 and, in use, provide improved pushability of the catheter. FIG. 5c is a cross-section of the catheter in FIG. 5a taken at line 5c-5c. In this embodiment, there are four longitudinal strips of EAP 20, with each strip of EAP 20 having a separate electrode 22 and there is a counter electrode 24. It is within the scope of the invention to have two, three, five, six, seven or eight longitudinal strips of EAP. Depending upon the number of strips of EAP used, the strips of EAP may wider or narrower than shown in FIG. 5c. The longitudinal strips of EAP 20 may extend from the proximal end region of the catheter to the proximal end of the balloon. In at least one embodiment, the strip of EAP is circumferential.

As shown in FIGS. 5a and 5c, the exterior surface of the strip of EAP 20 is substantially flush with the exterior surface of the catheter shaft. Similarly, except for the portion of EAP 20 that is deposited upon the electrode 22, the interior surface of the strip of EAP 20 is substantially flush with the interior surface of the catheter shaft. In at least one embodiment, the strip of EAP may form only a portion of the wall of the catheter shaft, i.e. the strip of EAP does not have the same thickness as the wall of the catheter shaft and is not flush with either the exterior surface or the interior surface of the shaft.

In the embodiment depicted in FIG. 6a, the catheter 30 has a section of EAP 20 that is actuated by an electrode 22 and counter electrode 24 which is in the form of a braid 60. The catheter has a proximal end 68 with a power source connector 66 which is connected to a power source. The power source connector 66 extends along the length of the catheter until it engages the electrode 22 ribbons of braid 60. Although the braid 60 is located near the distal end of the catheter proximal to the catheter tip 42, the braid 60 may be positioned anywhere along the length of the catheter wherever the section of EAP 20 is located. In at least one embodiment, the catheter shaft has a plurality of sections of EAP, at least one of the plurality of sections of EAP actuated by a braided electrode/counter-electrode. The braid 60 in this embodiment is engaged to the exterior surface of the catheter 30, thereby contacting the section of EAP 20. In at least one embodiment, the section of EAP 20 is a layer that is engaged to the surface of the catheter shaft. In at least one embodiment, a longitudinal section of the catheter shaft is made from EAP 20. In at least one embodiment, the braid 60 is engaged to the interior surface of the outer shaft. In at least one embodiment, the braid 60 is engaged to the exterior surface of the inner shaft. In at least one embodiment, the braid 60 is engaged to the interior surface of the inner shaft. In at least one embodiment, the braid 60 forms a part of the wall of the catheter shaft. In at least one embodiment, there is a solid electrolyte liner which is in contact with at least a portion of the section of EAP 20 and a portion of the counter electrode.

The braid 60 consists of at least three fibers or ribbons, as illustrated in FIGS. 6b and c. Some of the fibers or ribbons are electrodes 22 and some of the fibers or ribbons are counter electrodes 24. In at least one embodiment, the electrode 22 and counter electrode 24 ribbons are aligned in one direction and alternate with each other, as illustrated in FIG. 6d. The ribbons aligned at an angle to the electrode 22 and counter electrode 24 ribbons are made from an insulating material 62. Desirably, this arrangement prevents the electrode 22 and counter electrode 24 from contacting each other. In at least one embodiment, EAP 20 surrounds the electrode 22 ribbon and EAP 20 surrounds the counter electrode 24 ribbon which are woven into a braid configuration. Desirably, the electrode 22 and counter electrode 24 are not in contact because EAP 20 surrounds both the electrode 22 and the counter electrode 24. A solid electrolyte liner 64 may be interposed between the counter electrode 24 and the EAP 20 that surrounds the counter electrode 24, as illustrated in a cross-section of a ribbon FIG. 6e. Although the cross-section of the ribbon in FIG. 6e shows the ribbon as having a rectangular shape, the ribbon can have any cross-sectional shape so long as the ribbon can be woven into a braid 60.

For any braid configuration of the electrode 22 and counter electrode ribbons 24, the power source connector 66 is in contact with the electrode 22 ribbons so that the current passes from the power source to the power source connector 66 to the electrode 22 ribbon where the current is transferred to the section of EAP 20 and then transferred out of the section of EAP 20 to the counter electrode 22.

FIG. 6b illustrates the braid 60 where the ribbons form a loose pattern while FIG. 6c illustrates the braid 60 where the ribbons form a dense pattern. The pattern or spacing of the ribbons of the braid 60 relative to one another depends upon what the section of EAP 20 does when actuated. Desirably, since the braid 60 is engaged to the section of EAP 20, the ribbons forming the braid 60 move with the section of EAP 20. Thus, if actuation of the section of EAP 20 causes the section of EAP 20 to either volumetrically contract or to decrease in longitudinal length, the ribbons of the braid 60 become closer together when the section of EAP 20 is in an actuated state. If actuation of the section of EAP 20 causes the section of EAP 20 to either volumetrically expand or to increase in longitudinal length, the ribbons of the braid 60 become farther apart when the section of EAP 20 is in an actuated state. In at least one embodiment, the braid 60 has a loose pattern in the non-actuated state and a dense pattern in an actuated state. In at least one embodiment, the longitudinal length of the braid 60 decreases when in an actuated state. In at least one embodiment, the braid 60 has a dense pattern in the non-actuated state and a looser pattern in the actuated state. In at least one embodiment, the longitudinal length of the braid 60 increases when in an actuated state.

FIGS. 7a-7e show different embodiments of the invention where the EAP 20 allows for better guide wire 36 movement and flexibility. In the embodiment illustrated in FIGS. 7a and b, the shaft of the catheter 30 has a longitudinal channel 56 that is bridged by a plurality of segments of EAP 20. The segments of EAP 20 can have any longitudinal length and can be positioned close to one another or farther apart. In the FIG. 7a, the segments of EAP 20 extend only a short longitudinal distance and are spaced a distance away from one another.

In FIG. 7a the segments of EAP 20 are in a non-actuated state while in FIG. 7b the segments of EAP 20 are in an actuated state. When the segments of EAP 20 are actuated, the segments of EAP 20 decrease in length thereby bringing the two edges of the shaft together and closing the longitudinal channel 56. Closing the longitudinal channel 56 decreases the diameter of the guide wire lumen 38. In at least one embodiment, the inner shaft 32 has the longitudinal channel 56 such that the larger diameter guide wire lumen 38 in the non-actuated state provides better guide wire 36 movement than the smaller diameter guide wire lumen 38 in the actuated state. The smaller diameter guide wire lumen 38 also has better column strength and the catheter has greater pushability. In at least one embodiment, the inner shaft of a balloon catheter has the longitudinal channel such that the larger diameter of the inner shaft in the non-actuated state decreases the volume of the inflation lumen while the smaller diameter of the inner shaft in the actuated state increases the volume of the inflation lumen, thereby allowing better deflation.

FIGS. 7c-e illustrate another embodiment with a variable diameter. In this embodiment, the shaft 30 has a first edge 70 and a second edge 72. The first and second edges 70, 72 each have a section of EAP 20 engaged thereto and extending along the entire length of the edges 70, 72. In an actuated state, the section of EAP 20 along the first edge 70 and the section of EAP 20 along the second edge 70 cause the edges 70, 72 to overlap one another such that the second edge 72 is positioned closer to the guide wire 36 or to the longitudinal axis of the shaft 30 and the first edge 70 is positioned farther away from the guide wire 36 or the longitudinal axis, as illustrated in FIGS. 7c and 7d. When the sections of EAP 20 are in a non-actuated state, the first and second edges 70, 72 change position such that the first edge 70 and the second edge 72 are engaged and the shaft is a circular tube, as illustrated in FIGS. 7e and 7f. In at least one embodiment, the first edge 70 decreases in circumferential length and the second edge 72 bends outward so that the second edge 72 engages the first edge 70.

In the embodiment depicted in FIGS. 8a and 8b, the section of EAP 20 is positioned in the distal end region of the outer shaft 34 of the catheter 30 near the balloon 42. In FIG. 8a, the section of EAP 20 is in an actuated state and in FIG. 8b, the section of EAP 20 is in a non-actuated state. The longitudinal length of the section of EAP 20 decreases when the section of EAP 20 is de-actuated state. The decrease in the longitudinal length of the section of EAP 20 causes a concomitant decrease in the longitudinal length of the outer shaft 34. Desirably this decrease in the longitudinal length of the outer shaft 34 pulls the balloon 42 in a proximal direction thereby becoming taut and desirably improving or decreasing the profile of the balloon 42. In use, decreasing the profile of the balloon 42 desirably improves the crossability of the balloon 42. Desirably, this would allow the use of shaft materials that could normally not be used because those increase in length when exposed to typical temperatures used in sterilization or manufacturing.

FIGS. 9 and 10 depict an embodiment with at least one section of EAP 20 positioned on the inner shaft of a medical device so that the medical device can be steered by the selective actuation of a section of EAP 20.

In FIGS. 9a-9d, the inner shaft 32 of a balloon catheter 30 has four sections of EAP 20 located on the portion of the inner shaft 32 which is encircled by the balloon 42. FIG. 9b is a cross-section of the catheter 30 in FIG. 9a taken at line 9-9. In this embodiment, the four sections of EAP 20 do not form a part of wall of the inner shaft 32 but instead are engaged to the exterior surface of the inner shaft 32. FIG. 9c is a cross-section of an alternate embodiment of the catheter 30 taken at line 9-9. In this embodiment, the four sections of EAP 20 form a part of wall of the inner shaft 32. The embodiments in both FIGS. 9b and 9c have electrodes 22 and a counter electrode 24 that allow separate actuation of the sections of EAP 20. FIG. 9c illustrates how the inner shaft 32 bends when one of the sections of EAP 20 is actuated due to the bending of the section of EAP 20. Thus, the balloon 42 can be steered in one of four directions by actuating one of the four sections of EAP 20. The balloon 42 may be either in an inflated state or an un-inflated state when the section of EAP 20 is actuated.

Although this embodiment shows the sections of EAP 20 positioned at the distal end region of the catheter 30, the sections of EAP 20 can be placed anywhere along the length of the catheter 30 where steering control is desired. In at least one embodiment, there are a plurality of positions along the length of the catheter 30 where there are sections of EAP 20 about the circumference of the catheter 30 that bend when actuated, thereby causing the catheter 30 to bend in the region of the actuated section of EAP 20.

FIG. 10*a* shows a catheter with a self expanding stent 44 engaged to the inner shaft 32 and kept in position by a stent bumper 46 and an exterior sheath 35. The portion of the inner shaft 32 to which the self-expanding stent 44 is engaged has at least one section of EAP 20, as illustrated in the cross-section in FIG. 10*b*. Like the section of EAP 20 in the embodiment illustrated in FIGS. 9*a-d*, the section of EAP 20 bends when actuated. Therefore, actuation of the at least one section of EAP 20 causes the deflection of the catheter tip 42 due to the close proximity of the section of EAP 20 to the catheter tip 42, thereby steering the catheter. In this embodiment, the inner shaft 32 has one section of EAP 20 about the circumference of the inner shaft 32. In one embodiment at least one section of EAP 20 is located about the circumference of the inner shaft 32.

In the embodiment depicted in FIG. 11*a*, the at least one section of EAP 20 forms a spiral about the exterior surface of the inner shaft 32. In one embodiment, the at least one section of EAP 20 forms a spiral about the exterior surface of the outer shaft 34. In at least one embodiment, the spiral section of EAP 20 is one continuous section of EAP 20. In at least one embodiment, there are several sections of EAP 20 which form an overall spiral pattern. In at least one embodiment, the at least one section of EAP 20 extends substantially the entire length of the catheter in a spiral pattern. In at least one embodiment, the at least one section of EAP 20 in a spiral pattern is positioned at the distal end section of the catheter, the region to which the balloon is engaged.

In this embodiment, the at least one spiral section of EAP 20 can be selectively actuated to cause forced curvature or straightening of the catheter shaft. In use, a balloon catheter often maintains its curvature after the balloon has been deflated. This may cause the catheter to interfere with the deployed stent while the catheter is being withdrawn. In at least one embodiment, selective actuation will resist or prevent the inner shaft from holding, adopting, or maintaining the curvature or shape of a vessel during withdrawal of the catheter.

FIGS. 12*a* and 12*b* depict an embodiment where actuation of the sections of EAP 20 causes a change in the spatial configuration of the catheter. FIG. 12*a* shows a cross section of a catheter shaft 36 that has two longitudinal sections of EAP 20. Each section of EAP 20 has an electrode 22. The counter electrode 24 is positioned on the outside of the catheter shaft 36. FIG. 12*b* shows how the configuration of the catheter shaft 36 changes from a round cross-section to a more oval cross-section when the EAP is actuated. Desirably, the actuation of the EAP 20 improves the steering of the catheter around corners or turns as the catheter traverses the vasculature.

The catheter shaft 36 shown in FIGS. 12*a* and 12*b* can be manufactured by co-extruding a removable nylon wire in the wall of the catheter shaft 36. After the nylon wire is pulled out the resulting shaft 36 can be coated with a conductive ink to form the electrode 22 and filled with an EAP 20 by electropolymerization. The counter electrode 24 can be a conductive ink on the outside of the catheter shaft 36.

In the embodiment depicted in FIGS. 13*a-c*, the guide wire 36 has two axial sections of EAP 20. It is also within the scope of the invention to have a plurality of axial sections of EAP 20. It is also within the scope of the invention for the guide wire 36 to have one, three, four, five, six, seven, eight, nine, ten or more sections of EAP 20. In at least one embodiment, the guide wire 36 has several segments along the length of the guide wire 36 where there are a plurality of sections of EAP 20.

As shown in FIG. 13*b*, each axial section of EAP 20 is deposited on one third of the circumference of the metallic guide wire 36. A counter electrode 24 is deposited or printed on an insulator 26 which is positioned on the guide wire 36 opposite from the section of EAP 20. FIG. 13*c* shows how the guide wire 36 can bend when the proximal lower section of EAP 20*a* is in an actuated state while the distal upper section of EAP 20*b* is in a non-actuated state. Actuation of the section of EAP 20*a* causes the guide wire 36 to bend in a direction that is opposite from where the section of EAP 20*a* coats the guide wire 36. Desirably, in use, these axial sections of EAP 20 will allow the physician to control the direction of the guide wire 36 and allow for better maneuvering within the body lumen.

In at least one embodiment, the guide wire 36 is a polymer heat shrink tube made from polyester (PET). A conductive ink, for example, but not limited to, a silver or gold ink from Erconinc can be deposited onto the PET film. Because lines of conductive ink can be made very fine, multiple conductor lines can be printed along the guide wire 36. At the position of the EAP actuator, a larger surface can be printed and the EAP 20 deposited.

In one embodiment, the longitudinal sections of EAP 20 are positioned on a guide catheter 50. As shown in FIG. 14, the guide catheter 50 has a first section of EAP 20*a* which is positioned in the first curve area 52 and a second section of EAP 20*b* which is positioned in the second curve area 54 of the guide catheter 50. Desirably, in use, the sections of EAP 20*a,b* can be actuated when the physician is having trouble engaging the guide catheter 50 in the ostium. Actuation can cause the sections of EAP 20*a,b* to either increase in length or decrease in length thereby changing the shape of the curve areas 52,54 of the guide catheter 50. If the section of EAP 20*a,b* increases in length when actuated, the curve area 52,54 of the guide catheter 50 bends and becomes more acute. If the section of EAP 20*a,b* decreases in length when actuated, the curve area 52,54 of the guide catheter 50 bends and becomes less acute. Note that the first section of EAP 20*a* and the second section of EAP 20*b* can be actuated separately from one another.

FIGS. 15*a* and *b* illustrate the distal portion of a catheter 30 with a selectively directional catheter tip 42. The catheter tip 42 has at least two sections of EAP 20 positioned about the circumference of the catheter tip 42. In at least one embodiment, the two sections of EAP 20 are positioned on opposite sides of the catheter tip 42. The sections of EAP 20 in FIG. 15*a* are in a non-actuated state while one of the two sections of EAP 20 in FIG. 15*b* is in an actuated state. When the section of EAP 20 is actuated, it decreases in length. The decrease in length of the actuated section of EAP 20 causes the opposite side of the catheter tip 42 with the section of EAP 20 in a non-actuated state to bend or curl, as shown in FIG. 15*b*.

FIGS. 15*c* and *d* depict the distal portion of a catheter 30 with a directional, selectively flexible, bumper tip 42. The catheter tip 42 has two circumferential bands of EAP 20*a,b* engaged to one another by a circumferential layer of EAP 20*c*. The circumferential layer of EAP 20*c* forms the inner surface of the catheter tip 42. Between the two circumferential bands of EAP 20a,b and surrounding the circumferential layer of EAP 20c is a circumferential band of very flexible rubber 58, for example, but not limited to urethane. When the circumferential layer of EAP 20c is actuated, it decreases in length, while actuation of the two circumferential bands of EAP 20a,b causes the circumferential bands of EAP 20a,b to increase in length. The proximal circumferential band of EAP 20a increases in length towards the distal end of the catheter tip 42 while the distal circumferential band of EAP 20b increases in length towards the proximal end of the catheter tip 42. The actuation of the two bands of EAP 20a,b squeezes the circumferential band of rubber 58 and causes the circumferential band of rubber 58 to bulge out and form a rubber bumper. The circumferential layer of EAP 20c directs the bulging of the squeezed circumferential band of rubber 58 outwards. Desirably, the rubber bumper 58 is able to deflect the distal end of the catheter tip 42 and prevent it from catching on the anatomy or other items within the body lumen, for example, a stent.

FIGS. 15e and f illustrate another embodiment of a catheter tip with a circumferential section of EAP 20. The section of EAP 20 is in a non-actuated state in FIG. 15e and in an actuated state in FIG. 15f. When the section of EAP 20 is actuated, the section of EAP 20 volumetrically expands.

In the embodiment shown in FIG. 16a, the at least one section of EAP 20 is in a non-actuated state and positioned at the distal end of the guide wire 36. In the embodiment shown in FIGS. 16a and b, the section of EAP 20 becomes circumferential at the distal end of the guide wire 36. When the section of EAP 20 is actuated, the EAP 20 bends in an axial direction, as shown in FIG. 16b. Desirably, this improves the manipulation and the maneuverability of the guide wire 36 and allows easier access to side branches, easier delivery through stent struts and easier manipulation through the desired vasculature. In at least one embodiment, the guide wire 36 has two separate sections of EAP 20 which can be actuated to maneuver the guide wire 36. In this embodiment, for example, one section of EAP 20 would bend to the right when actuated while the other section of EAP 20 would bend to the left when actuated.

FIG. 17 depicts an embodiment wherein a layer of EAP 20 on the guide wire 36 is applied to the guide wire 36 while the guide wire 36 is experiencing torsional forces. In this embodiment, the guide wire 36 is subjected to slight rotational torque between the distal and the proximal ends of the guide wire 36. While the guide wire 36 is subjected to this rotational torque, a layer of EAP 20 is applied to the complete circumference of the guide wire 36 with the exception of some small sections which have a counter electrode 24 deposited upon an insulator 26. After the layer of EAP 20 is deposited on the guide wire 36, the torque on the guide wire 36 can be released. At this point the shaft of the guide wire 36 will rotate back to its original non-twisted state and the layer of EAP 20 will have a torsion force upon it. In essence, there is a torque balance between the shaft of the guide wire 36 and the layer of EAP 20. When the layer of EAP 20 is actuated, the torque balance is shifted between the EAP 20 and the guide wire 36 and results in a net rotation of the shaft of the guide wire 36. If the tip is bended, actuation of the layer of EAP 20 on the shaft of the guide wire 36 allows a physician to steer the tip around its axis.

The shafts of the catheters of the present invention are manufactured from any suitable material to impart the desired characteristics and EAPs. Examples of suitable materials include, but are not limited to, polymers such as polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysulfone, nylon, perfluoro (propyl vinyl ether) (PFA), polyether-ester, polymer/metal composites, etc., or mixtures, blends or combinations thereof. One example of a suitable polyether block ester is available under the trade name ARNITEL, and one suitable example of a polyether block amide (PEBA) is available under the trade name PEBAX®, from ATOMCHEM POLYMERS, Birdsboro, Pa.

The catheters of the present invention are actuated, at least in part, using EAP actuators. EAPs are characterized by their ability to change shape in response to electrical stimulation. EAPs include electric EAPs and ionic EAPs. Piezoelectric materials may also be employed but tend to undergo small deformation when voltage is applied.

Electric EAPs include ferroelectric polymers, dielectric EAPs, electrorestrictive polymers such as the electrorestrictive graft elastomers and electro-viscoelastic elastomers, and liquid crystal elastomer materials.

Ionic EAPs include ionic polymer gels, ionomeric polymer-metal composites, conductive polymers and carbon nanotubes. Upon application of a small voltage, ionic EAPs can bend significantly. Ionic EAPs also have a number of additional properties that make them attractive for use in the devices of the present invention, including the following: (a) they are lightweight, flexible, small and easily manufactured; (b) energy sources are available which are easy to control, and energy can be easily delivered to the EAPs; (c) small changes in potential (e.g., potential changes on the order of 1V) can be used to effect volume change in the EAPs; (d) they are relatively fast in actuation (e.g., full expansion/contraction in a few seconds); (e) EAP regions can be created using a variety of techniques, for example, electrodeposition; and (f) EAP regions can be patterned, for example, using photolithography, if desired.

Conductive plastics may also be employed. Conductive plastics include common polymer materials which are almost exclusively thermoplastics that require the addition of conductive fillers such as powdered metals or carbon (usually carbon black or fiber).

Ionic polymer gels are activated by chemical reactions and can become swollen upon a change from an acid to an alkaline environment.

Ionomeric polymer-metal composites can bend as a result of the mobility of cations in the polymer network. Suitable base polymers include perfluorosulfonate and perfluorocarboxylate.

Essentially any EAP that exhibits contractile or expansile properties may be used in connection with the various active regions of the invention, including any of those listed above.

In some embodiments herein, the EAPs employed are ionic EAPs, more specifically, the ionic EAPs are conductive polymers that feature a conjugated backbone (they include a backbone that has an alternating series of single and double carbon-carbon bonds, and sometimes carbon-nitrogen bonds, i.e. n-conjugation) and have the ability to increase the electrical conductivity under oxidation or reduction. For polymers allow freedom of movement of electrons, therefore allowing the polymers to become conductive. The pi-conjugated polymers are converted into electrically conducting materials by oxidation (p-doping) or reduction (n-doping).

The volume of these polymers changes dramatically through redox reactions at corresponding electrodes through exchanges of ions with an electrolyte. The EAP-containing active region contracts or expands in response to the flow of ions out of, or into, the same. These exchanges occur with small applied voltages and voltage variation can be used to control actuation speeds.

Any of a variety of pi-conjugated polymers may be employed herein. Examples of suitable conductive polymers include, but are not limited to, polypyrroles, polyanilines, polythiophenes, polyethylenedioxythiophenes, poly(p-phenylenes), poly(p-phenylene vinylene)s, polysulfones, polypyridines, polyquinoxalines, polyanthraquinones, poly(N-vinylcarbazole)s and polyacetylenes, with the most common being polythiophenes, polyanilines, and polypyrroles.

Some of the structures are shown below:

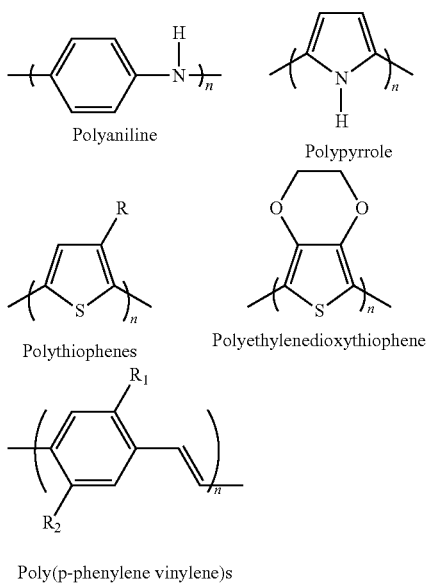

Polypyrrole, shown in more detail below, is one of the most stable of these polymers under physiological conditions:

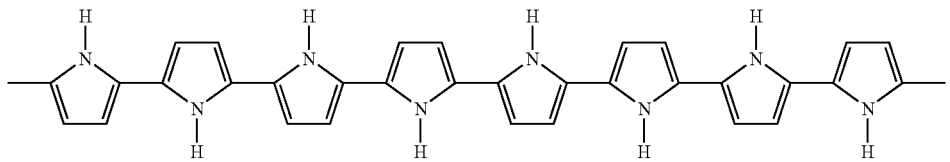

The above list is intended for illustrative purposes only, and not as a limitation on the scope of the present invention.

The behavior of conjugated polymers is dramatically altered with the addition of charge transfer agents (dopants). These materials can be oxidized to a p-type doped material by doping with an anionic dopant species or reducible to a n-type doped material by doping with a cationic dopant species. Generally, polymers such as polypyrrole (PPy) are partially oxidized to produce p-doped materials:

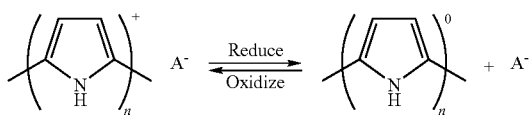

Dopants have an effect on this oxidation-reduction scenario and convert semi-conducting polymers to conducting versions close to metallic conductivity in many instances. Such oxidation and reduction are believed to lead to a charge imbalance that, in turn, results in a flow of ions into or out of the material. These ions typically enter/exit the material from/into an ionically conductive electrolyte medium associated with the EAP.

Dimensional or volumetric changes can be effectuated in certain polymers by the mass transfer of ions into or out of the polymer. This ion transfer is used to build conductive polymer actuators (volume change). For example, in some conductive polymers, expansion is believed to be due to ion insertion between chains, whereas in others inter-chain repulsion is believed to be the dominant effect. Regardless of the mechanism, the mass transfer of ions into and out of the material leads to an expansion or contraction of the polymer, delivering significant stresses (e.g., on the order of 1 MPa) and strains (e.g., on the order of 10%). These characteristics are ideal for construction of the devices of the present invention. As used herein, the expansion or the contraction of the active region of the device is generally referred to as "actuation."

The following elements are commonly utilized to bring about EAP actuation: (a) a source of electrical potential, (b) an active region, which comprises the EAP, (c) a counter electrode and (d) an electrolyte in contact with both the active region and the counter electrode.

The source of electrical potential for use in connection with the present invention can be quite simple. In at least one embodiment, for example, the source of electric current may consist of a dc battery and an on/off switch. Alternatively, more complex systems can be utilized. In at least one embodiment, for example, an electrical link can be established with a microprocessor, allowing a complex set of control signals to be sent to the EAP-containing active region(s). Other embodiments of the invention however may utilize any of a variety of electrical sources and configurations for regulating the electric current to the EAP.

The electrolyte, which is in contact with at least a portion of the surface of the active region, allows for the flow of ions and thus acts as a source/sink for the ions. Any suitable electrolyte may be employed herein. The electrolyte may be, for example, a liquid, a gel, or a solid, so long as ion movement is permitted. Examples of suitable liquid electrolytes include, but are not limited to, an aqueous solution containing a salt, for example, a NaCl solution, a KCl solution, a sodium dodecylbenzene sulfonate solution, a phosphate buffered solution, physiological fluid, etc. Examples of suitable gel electrolytes include, but are not limited to, a salt-containing agar gel or polymethylmethacrylate (PMMA) gel. Solid electrolytes include ionic polymers different from the EAP and salt films.

The counter electrode may be formed from any suitable electrical conductor, for example, a conducting polymer, a conducting gel, or a metal, such as stainless steel, gold or platinum. At least a portion of the surface of the counter electrode is generally in contact with the electrolyte, in order to provide a return path for charge.

In one specific embodiment, the EAP employed is polypyrrole. Polypyrrole-containing active regions can be fabricated using a number of known techniques, for example, extrusion, casting, dip coating, spin coating, or electro-polymerization/deposition techniques. Such active regions can also be patterned, for example, using lithographic techniques, if desired.

As a specific example of a fabrication technique, polypyrrole can be galvanostatically deposited on a platinised substrate from a pyrrole monomer solution using the procedures described in D. Zhou et al., "Actuators for the Cochlear Implant," Synthetic Metals 135-136 (2003) 39-40. Polypyrrole can also be deposited on gold. In some embodiments, adhesion of the electrodeposited polypyrrole layer is enhanced by covering a metal such as gold with a chemisorbed layer of molecules that can be copolymerized into the polymer layer with chemical bonding. Thiol is one example of a head group for strong chemisorbtion to metal. The tail group may be chemically similar to structured groups formed in the specific EAP employed. The use of a pyrrole ring attached to a thiol group (e.g., via a short alkyl chain) is an example for a polypyrrole EAP. Specific examples of such molecules are 1-(2-thioethyl)-pyrrole and 3-(2-thioethyl)-pyrrole. See, e.g., E. Smela et al., "Thiol Modified Pyrrole Monomers: 1. Synthesis, Characterization, and Polymerization of 1-(2-Thioethyl)-Pyrrole and 3-(2-Thioethyl)-Pyrrole," *Langmuir,* 14 (11), 2970-2975, 1998.

Various dopants, including large immobile anions and large immobile cations, can be used in the polypyrrole-containing active regions. According to one specific embodiment, the active region comprises polypyrrole (PPy) doped with dodecylbenzene sulfonate (DBS) anions. When placed in contact with an electrolyte containing small mobile cations, for example, Na$^+$ cations, and when a current is passed between the polypyrrole-containing active region and a counter electrode, the cations are inserted/removed upon reduction/oxidation of the polymer, leading to expansion/contraction of the same. This process can be represented by the following equation:

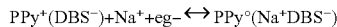

$$PPy^+(DBS^-) + Na^+ + eg- \leftrightarrow PPy°(Na^+DBS^-)$$

where Na$^+$ represents a sodium ion, e$^-$ represents an electron, PPy$^+$ represents the oxidized state of the polypyrrole, PPy° represents the reduced state of the polymer, and species in parentheses indicate that they are incorporated into the polymer. In this case the sodium ions are supplied by the electrolyte that is in contact with the EAP member. Specifically, when the EAP is oxidized, the positive charges on the backbone are at least partially compensated by the DBS$^-$ anions present within the polymer. Upon reduction of the polymer, however, the immobile DBS$^-$ ions cannot exit the polymer to maintain charge neutrality, so the smaller, more mobile, Na$^+$ ions enter the polymer, expanding the volume of the same. Upon re-oxidation, the Na$^+$ ions again exit the polymer into the electrolyte, reducing the volume of the polymer.

EAP-containing active regions can be provided that either expand or contract when an applied voltage of appropriate value is interrupted depending, for example, upon the selection of the EAP, dopant, and electrolyte.

Additional information regarding EAP actuators, their design considerations, and the materials and components that may be employed therein, can be found, for example, in E. W. H. Jager, E. Smela, O. Inganäs, "Microfabricating Conjugated Polymer Actuators," *Science,* 290, 1540-1545, 2000; E. Smela, M. Kallenbach, and J. Holdenried, "Electrochemically Driven Polypyrrole Bilayers for Moving and Positioning Bulk Micromachined Silicon Plates," *J. Microelectromechanical Systems,* 8(4), 373-383, 1999; U.S. Pat. No. 6,249,076, assigned to Massachusetts Institute of Technology, and Proceedings of the SPIE, Vol. 4329 (2001) entitled "Smart Structures and Materials 2001: Electroactive Polymer and Actuator Devices (see, e.g., Madden et al, "Polypyrrole actuators: modeling and performance," at pp. 72-83), each of which is hereby incorporated by reference in its entirety.

Furthermore, networks of conductive polymers may also be employed. For example, it has been known to polymerize pyrrole in EAP networks such as poly(vinylchloride), poly(vinyl alcohol), NAFION®, a perfluorinated polymer that contains small proportions of sulfonic or carboxylic ionic functional groups, available from E.I. DuPont Co., Inc. of Wilmington, Del.

EAPs are also discussed in detail in U.S. Patent Application Publications 2004/0143160 and 2004/0068161 and commonly assigned copending U.S. patent application Ser. No. 10/763,825, the entire content of both are incorporated by reference herein.

In some embodiments the catheter may include one or more areas, bands, coatings, members, etc. that is (are) detectable by imaging modalities such as X-Ray, MRI, ultrasound, etc. In some embodiments at least a portion of the catheter is at least partially radiopaque.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A method of forming an actuatable medical device, the method comprising:
    forming a medical device with a first wire by coextruding a first device material and a first wire material;
    pulling the first wire from the medical device to form a first channel;
    placing an electrode in the first channel;
    placing an actuatable polymer in the first channel, the actuatable polymer covering the electrode; and providing a counter electrode on a first surface of the medical device.

2. The method of claim 1, the actuable medical device being a catheter, the catheter comprising a shaft, the shaft comprising the first channel.

3. The method of claim 1, further comprising:
pulling a second wire from the medical device to form a second channel;
placing an electrode in the second channel;
placing an actuatable polymer in the second channel, the actuatable polymer covering the electrode.

4. A method of manufacturing a medical device comprising:
forming the medical device with a first removable wire by coextruding a first device material and a first wire material to form a wall with a first surface and the first removable wire;
pulling the first removable wire from the wall to form a first channel in the wall of the medical device;
placing an electrode in the first channel;
placing an actuatable polymer in the first channel, the actuatable polymer covering the electrode; and
providing a counter electrode on the first surface of the wall.

5. The method of claim 4, wherein the medical device is a catheter and the wall forms at least a portion of a shaft of the catheter.

6. The method of claim 5, wherein the shaft defines a lumen.

7. The method of claim 4, wherein the electrode is a conductive ink, the conductive ink coating a portion of the channel.

8. The method of claim 4, wherein the actuatable polymer is placed in the first channel by electropolymerization.

9. The method of claim 4, wherein the actuatable polymer forms at least one first portion of the first surface of the wall.

10. The method of claim 9, the wall having at least one second portion of the first surface of the wall, the counter electrode being placed on the at least one second portion of the first surface.

11. The method of claim 4, wherein the actuatable polymer is an electroactive polymer.

12. The method of claim 4, wherein the counter electrode is conductive ink.

13. The method of claim 4, the first channel being parallel to a longitudinal axis of the medical device.

14. The method of claim 4, wherein the removable wire is a nylon wire.

15. The method of claim 4, the first surface being an outer surface of the wall.

16. A method of manufacturing a catheter shaft, the catheter shaft having an outer surface, the method comprising:
coextruding shaft material with nylon to form the catheter shaft with a removable nylon wire;
creating a void by pulling the nylon wire from the catheter shaft, the void having a surface;
coating a portion of the surface of the void with a conductive ink, the conductive ink forming an electrode;
placing electroactive polymer into the void; and
coating a portion of the outer surface of the catheter shaft with a conductive ink, the conductive ink forming a counter electrode.

17. The method of claim 16, the electroactive polymer being placed into the void by electropolymerization.

18. The method of claim 16, the electroactive polymer in the void forming a portion of the outer surface of the catheter shaft.

19. The method of claim 16, the catheter shaft defining a lumen.

* * * * *